US009656092B2

(12) United States Patent
Golden

(10) Patent No.: US 9,656,092 B2
(45) Date of Patent: May 23, 2017

(54) METHODS AND SYSTEMS FOR MANAGING, CONTROLLING AND MONITORING MEDICAL DEVICES VIA ONE OR MORE SOFTWARE APPLICATIONS FUNCTIONING IN A SECURE ENVIRONMENT

(75) Inventor: Michael Golden, Greensburg, PA (US)

(73) Assignee: Chronicmobile, Inc.

(*) Notice: Subject to any disclaimer, the term of this patent is extended or adjusted under 35 U.S.C. 154(b) by 699 days.

(21) Appl. No.: 12/779,025

(22) Filed: May 12, 2010

(65) Prior Publication Data
US 2010/0292556 A1    Nov. 18, 2010

Related U.S. Application Data

(60) Provisional application No. 61/177,495, filed on May 12, 2009.

(51) Int. Cl.
| | | |
|---|---|---|
| *A61N 1/372* | (2006.01) | |
| *G06F 19/00* | (2011.01) | |
| *G06Q 10/06* | (2012.01) | |
| *G06Q 50/22* | (2012.01) | |
| *A61B 5/00* | (2006.01) | |

(52) U.S. Cl.
CPC ........ *A61N 1/37282* (2013.01); *A61B 5/7465* (2013.01); *A61N 1/37235* (2013.01); *G06F 19/3412* (2013.01); *G06F 19/3418* (2013.01); *G06Q 10/06* (2013.01); *G06Q 50/22* (2013.01); *A61B 5/0002* (2013.01)

(58) Field of Classification Search
USPC .......................................... 705/2–3; 600/300
See application file for complete search history.

(56) References Cited

U.S. PATENT DOCUMENTS

| | | | | |
|---|---|---|---|---|
| 2004/0122488 | A1* | 6/2004 | Mazar ............... | A61N 1/37235 607/60 |
| 2008/0040788 | A1* | 2/2008 | Steinkogler ......... | G06F 19/3418 726/11 |

(Continued)

FOREIGN PATENT DOCUMENTS

KR    1020070021746 A    2/2007

OTHER PUBLICATIONS

U.S. Appl. No. 12/239,906, filed Sep. 29, 2008.

(Continued)

*Primary Examiner* — Fonya Long
*Assistant Examiner* — Rajiv Raj
(74) *Attorney, Agent, or Firm* — Cooley LLP

(57) ABSTRACT

Systems and methods that include configurations of a medical device, user device and service platform are described. Embodiments may include a secure network to run medical applications that control and/or monitor the medical device. An online store may be provided for storing and distributing medical applications to the user device and medical device. A secure environment may be provided within the user device and medical device that protects the integrity of medical applications running on those devices. A service platform may provide a service that enables a medical authority to certify and monitor the medical applications. In some implementations, various third parties and the user of the user device may be allowed to manage and monitor the medical device.

31 Claims, 16 Drawing Sheets

(56) References Cited

U.S. PATENT DOCUMENTS

| | | | |
|---|---|---|---|
| 2008/0103554 A1* | 5/2008 | Dicks | G06F 19/3418 607/60 |
| 2008/0178144 A1* | 7/2008 | Bazigos | G06F 11/3604 717/101 |
| 2008/0301665 A1 | 12/2008 | Charlton et al. | |
| 2009/0088607 A1* | 4/2009 | Muraca | A61B 5/0002 600/300 |

OTHER PUBLICATIONS

PCT/US2010/034620 International Search Report and Written Opinion mailed Jan. 5, 2011.
PCT/US2010/034620 Written Opinion mailed Jan. 5, 2011.

* cited by examiner

METHODS AND SYSTEMS FOR MANAGING, CONTROLLING AND MONITORING MEDICAL DEVICES VIA ONE OR MORE SOFTWARE APPLICATIONS FUNCTIONING IN A SECURE ENVIRONMENT

CROSS-REFERENCE TO RELATED APPLICATIONS

This application claims priority under 35 U.S.C. §119(e) to U.S. Provisional Patent Application Ser. No. 61/177,495, entitled METHODS AND SYSTEMS FOR MANAGING, CONTROLLING AND MONITORING MEDICAL DEVICES VIA ONE OR MORE SOFTWARE APPLICATIONS FUNCTIONING IN A SECURE ENVIRONMENT, filed on May 12, 2009, the content of which is incorporated by reference herein for all purposes.

FIELD OF THE INVENTION

The present invention is directed generally to systems for interacting with medical devices. More particularly, but not exclusively, embodiments may include methods and systems for managing, controlling and monitoring medical devices via a software application functioning in a secure environment as well as associated networks for delivering approved software applications to a user device, with the application then enabling the user device to exchange information with a medical device near, carried on or implanted in a patient.

BACKGROUND

Medical technology can improve and even prolong people's lives, while reducing long-term health costs associated with complications and long-term health care, particularly for those with chronic diseases. Unfortunately, use of such medical technology may be costly and inconvenient. For example, a patient/user may be required to have a medical device implanted, worn, carried or otherwise maintained near their person. Alternatively or in addition, the user and/or personnel of an institution (e.g., hospital, personal care home, nursing home, etc) may need to maintain an additional device (a "medical controller") for purposes of, e.g., monitoring, controlling, reading from, or updating information to the aforementioned medical device.

Because of strict regulatory requirements imposed on medical devices, such medical controllers typically require a substantial amount of time, money and risk to design, develop, test, validate, certify, manufacture, inventory, distribute, upgrade and receive reimbursement. When compared to the more rapid development pace of general user devices (e.g., mobile devices, laptops, personal computers, etc), medical controllers tend to be technically inferior in relation to, among other things, processor speed, amount of memory, screen type and resolution, connectivity, security as well as other operational and performance characteristics.

Much of a user device's design, development, testing, validation, certification, manufacturing, inventory, distribution, upgrade capabilities and processes and reimbursement/subsidization are already managed by various parties. For example, parties that manage these aspects in a mobile device ecosystem include phone OEMs, distributors, wireless carriers, network operators, application developers as well as others. However, mass-market mobile devices have not been permitted to play the roll of a medical controller due to several considerations, including but not limited to:

1) Technological constraints such as local radio frequency (RF) technology (e.g. Bluetooth, Bluetooth LE, Zigbee, ANT, MICS, MEDS, WiFi, Peanut, etc.) utilized by a mobile device and the power consumption required for communication with a medical device and 2) Safety and privacy constraints relating to requirements of, for example, the Food and Drug Administration (FDA) and the Health Insurance Portability and Accountability Act (HIPAA).

Accordingly, there is a need in the art for enhanced methods and systems to address these problems as well as others.

SUMMARY

This application is directed generally to systems for interacting with medical devices.

In one aspect, the invention is directed to a computer-implemented method of interacting with a medical device in conjunction with a user device, comprising: receiving, at the user device, a certified medical application; storing the certified medical application in a secure memory segment of the user device, wherein the secure memory segment is configured to be isolated from a nonsecure memory segment of the user device and wherein the nonsecure memory segment is configured to store one or more noncertified applications; and initiating establishment of a communication link from the user device to the medical device, wherein the communication link is configured to facilitate execution of the certified medical application. The method may further include sending, to the medical device, one or more instructions for execution on the medical device to implement a medical control or monitoring function, and the method may further include receiving, from the medical device, a set of data associated with a control or monitoring function implemented on the medical device, and storing, in the secure memory segment, the set of data. The set of data may be encrypted prior to storing.

In another aspect, the invention is directed to a computer implemented method of operating a medical device, comprising: initiating establishment of a communications connection between a user device and the medical device; sending, from a secure segment of the user device to the medical device, via the communications connection, instructions for controlling or monitoring an operational function of the medical device; receiving, from the medical device, data associated with operation of the medical device; and storing the data associated with operation of the medical device in the secure segment. The sending may be initiated from a certified medical application and the data is received by a certified medical application. The method may further include sending, from the user device, the data associated with operation of the medical device to a service platform. The sending may further include sending a certified medical application to the medical device. The certified medical application may be received at the user device, from a service platform, in a secure environment of the user device, and stored in the secure segment.

In another aspect, the invention is directed to an apparatus for use in a user device, comprising: one or more processors configured to be coupled to a network communication interface and a medical device communication interface; and a memory coupled to the one or more processors, said memory configured to include: an unsecured segment; and a secure segment logically separated from the unsecured segment, wherein the secured segment is configured to securely store a certified medical application disposed for execution on the processor to facilitate control and/or monitoring of a medical device. The secure segment may be further configured to securely store a set of data provided from the medical device, and the memory may further includes a secure communication application configured to receive, from a service platform, a certified medical application and store the certified medical application in the secure segment. The secure communication application may be further configured to verify, in response to receipt of the medical application, that the received medical application has been approved for operation with the medical device by a regulatory authority. The regulatory authority may be the FDA.

In another aspect, the present invention is directed to a method of provisioning medical applications to a user device, comprising: receiving, from a medical application developer, a first medical application, wherein the first medical application is configured to operate a specific medical device subject to a regulatory certification; storing, in a computer system, the first medical application; providing the first medical application to a regulatory authority for certification of the first medical application in conjunction with the specific medical device; receiving, from the regulatory authority, a certified version of the first medical application; and storing the certified version of the first medical application in a certified medical application repository. The method may further include providing the certified version of the first medical application to a user device via an electronic communications interface, wherein the user device is configured to communicate with the medical device to facilitate medical device operation. The method may also include testing, prior to the providing the first medical application to a regulatory authority, the first medical application for compliance with one or more statutory or regulatory requirements. The method may further include providing the certified first medical application to an online applications store. The medical device may be an infusion pump, a pacemaker, a defibrillator, a heart monitor, a heart control device, a blood glucose monitor, a continuous blood glucose monitor, a pulse sensor, an oxygen saturation sensor or another medical device as described herein or known or developed in the art.

In another aspect, the present invention is directed to a medical device, comprising: a medical monitoring or control apparatus disposed to monitor or control a patient medical function; a network communication interface; one or more processors configured to be coupled to the network communication interface and the medical monitoring or control apparatus; and a memory coupled to the one or more processors, said memory configured to include: an unsecured segment; and a secure segment logically separated from the unsecured segment, wherein the secured segment is configured to securely store a certified medical application disposed for execution on the processor to facilitate control and/or monitoring of the medical monitoring or control apparatus. The secure segment may be further configured to securely store a set of data provided from the medical monitoring or control apparatus. The memory may further include a secure communication application configured to receive, from a service platform, a certified medical application and store the certified medical application in the secure segment. The secure communication application may be further configured to verify, in response to receipt of the medical application, that the received certified medical application has been approved for operation with the medical device by a regulatory authority. The regulatory authority may be the FDA and the certified medical application may be certified by the FDA.

Additional aspects of the present invention are described below in conjunction with the appended Drawings.

BRIEF DESCRIPTION OF THE DRAWINGS

Various objects and advantages and a more complete understanding of the invention are apparent and more readily appreciated by reference to the following Detailed Description and to the appended claims when taken in conjunction with the accompanying Drawings wherein:

DETAILED DESCRIPTION

Figure 1:
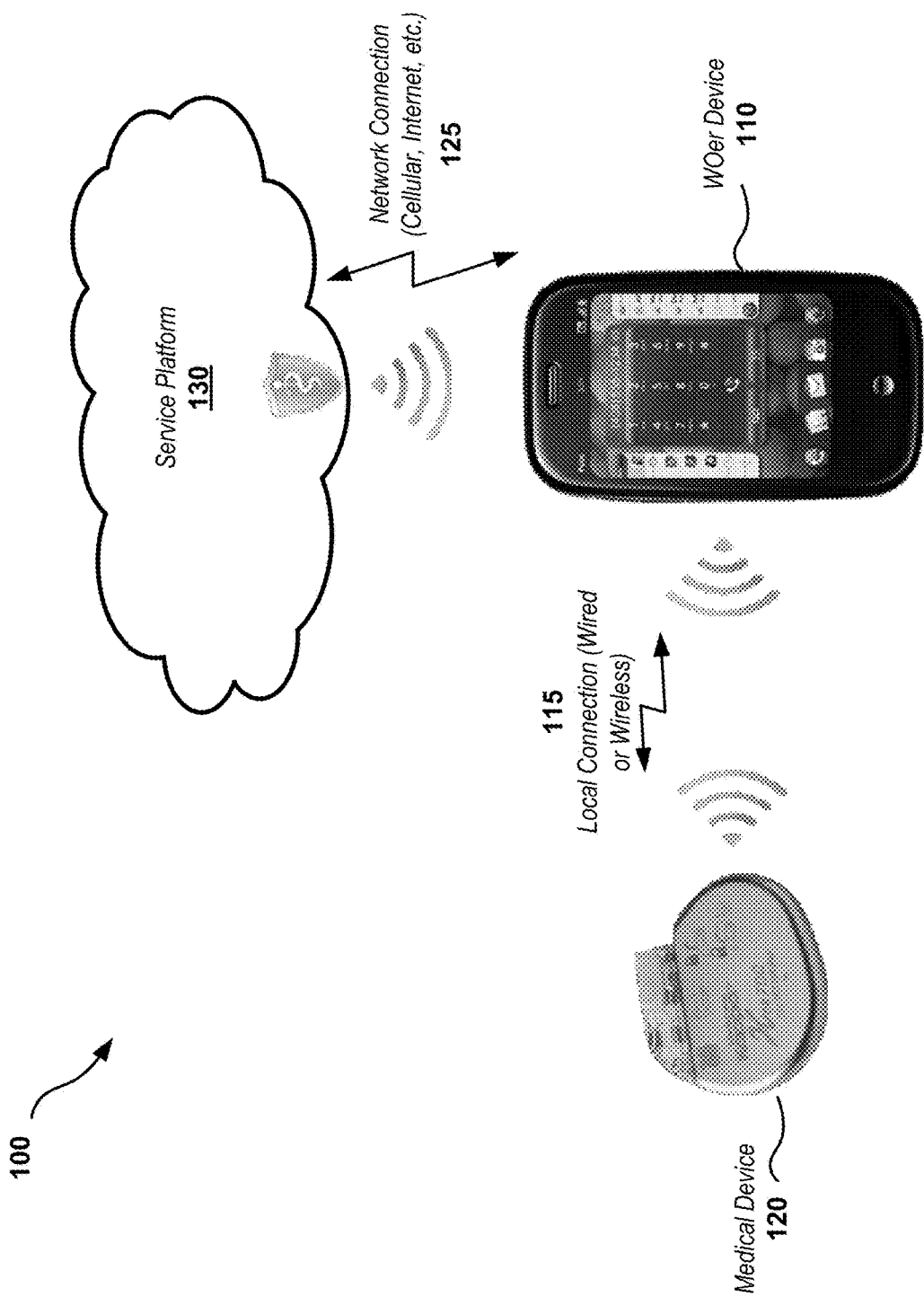
FIG. 1 depicts an embodiment of a network 100 for managing and monitoring medical devices via a software application functioning in a secure environment in accordance with aspects of the present invention.

The embodiments described below are provided for purposes of illustrating various features and functionality of the present invention. It is to be understood, however, that there is no intention to limit the invention to the forms described in the Detailed Description. One skilled in the art can recognize that there are numerous modifications, equivalents and alternative constructions that fall within the spirit and scope of the invention as described and illustrated herein and as expressed in the claims.

In one aspect, embodiments of the invention may provide systems and methods for downloading an application from a web-based server to a user device, wherein the application is downloaded to a secure environment within the user device. The secure environment may be used to facilitate control of the processes and functions described in further detail below to facilitate application quality control, regulatory compliance, security and other related features and functions.

In another aspect, embodiments of the invention may provide systems and methods for running at least part of an application within a secure environment of a user device, wherein the application manages, controls and/or monitors a medical device configured to be in communication with the user device.

In another aspect, embodiments of the invention may provide systems and methods for uploading data and/or an application to or from a web-based server or client, wherein the application may be made available to various network devices that may include a user device, a medical authority, an application developer, and/or other third parties. This access to other network devices may be done in a secure, controlled fashion so at to comply with regulatory requirements and/or statutory requirements such as HIPAA requirements.

In another aspect, embodiments of the invention may provide systems and methods wherein a user device, third party computing device and/or web-based server operates as a gateway via which a medical device receives and/or sends information. This may be done in conjunction with a user device. This gateway functionality may be done in a secure, controlled fashion so at to comply with regulatory requirements and/or statutory requirements such as HIPAA requirements.

In another aspect, embodiments of the invention may provide systems and methods wherein a user device, third party computing device and/or web-based server executes an application, thereby controlling a medical device in relation to the execution of the application. This may be done in conjunction with a user device. This functionality may be done in a secure, controlled fashion so at to comply with regulatory requirements and/or statutory requirements such as HIPAA requirements.

In another aspect, embodiments of the invention may provides systems and methods wherein a user device, third party computing device and/or web-based server executes an application, thereby monitoring a medical device in relation to the execution of the application. This functionality may be done in a secure, controlled fashion so at to comply with regulatory requirements and/or statutory requirements such as HIPAA requirements.

In another aspect, embodiments of the invention may provide enhanced functionality medical devices to allow them to interface with networks by incorporated functionality traditionally associated with user devices such as cellular phones. Some of these embodiments may incorporate this functionality as a thin client into the medical device to allow it to receive and/or send certified medical applications, updated applications, user/patient data, as well as other applications or information. This may be done by using widely availably infrastructure such as the cellular network and/or Internet.

One embodiment includes a computer-implemented method of interacting with a medical device in conjunction with a user device, comprising receiving, at the user device, a certified medical application; storing the certified medical application in a secure memory segment of the user device, wherein the secure memory segment is configured to be isolated from a nonsecure memory segment of the user device and wherein the nonsecure memory segment is configured to store one or more noncertified applications; and initiating establishment of a communication link from the user device to the medical device, wherein the communication link is configured to facilitate execution of the certified medical application. The method may further comprise sending, to the medical device, one or more instructions for execution on the medical device to implement a medical control or monitoring function and the method may further comprise receiving, from the medical device, a set of data associated with a control or monitoring function implemented on the medical device, and storing, in the secure memory segment, the set of data. The set of data may be encrypted prior to storing.

The method may also include sending, from the user device to a service platform, the set of data, and encrypting the set of data prior to the sending the set of data.

The method may further comprise verifying that the certified medical application conforms to one or more regulatory requirements, and the verifying may include validating that the certified medical application conforms to a Food and Drug Administration (FDA) medical device compliance regulation.

Another embodiment of the invention includes a computer implemented method of operating a medical device, comprising initiating establishment of a communications connection between a user device and the medical device; sending, from a secure segment of the user device to the medical device, via the communications connection, instructions for controlling or monitoring an operational function of the medical device; receiving, from the medical device, data associated with operation of the medical device; and storing the data associated with operation of the medical device in the secure segment. The sending may be initiated from a certified medical application and the data may be received by a certified medical application.

The method may further include sending, from the user device, the data associated with operation of the medical device to a service platform. The sending may further include sending a certified medical application to the medical device. The certified medical application may be received at the user device, from a service platform, in a secure environment of the user device, and stored in the secure segment.

Another embodiment of the invention includes an apparatus for use in a user device, comprising: one or more processors configured to be coupled to a network communication interface and a medical device communication interface; and a memory coupled to the one or more processors, said memory configured to include: an unsecured segment; and a secure segment logically separated from the unsecured segment, wherein the secured segment is configured to securely store a certified medical application disposed for execution on the processor to facilitate control and/or monitoring of a medical device. The secure segment may be further configured to securely store a set of data provided from the medical device, and the memory may further includes a secure communication application configured to receive, from a service platform, a certified medical application and store the certified medical application in the secure segment.

The secure communication application may be further configured to verify, in response to receipt of the medical application, that the received medical application has been approved for operation with the medical device by a regulatory authority. The regulatory authority may be the FDA.

The apparatus may include two processor cores and wherein a first of the two processor cores is coupled to the unsecure segment and the second of the two processor cores is coupled to the secure segment. The first processor core and the second processor core may be isolated from each other.

Another embodiment may include a method of provisioning medical applications to a user device, comprising: receiving, from a medical application developer, a first medical application, wherein the first medical application is configured to operate a specific medical device subject to a regulatory certification; storing, in a computer system, the first medical application; providing the first medical application to a regulatory authority for certification of the first medical application in conjunction with the specific medical device; receiving, from the regulatory authority, a certified version of the first medical application; and storing the certified version of the first medical application in a certified medical application repository.

The method may further include providing the certified version of the first medical application to a user device via an electronic communications interface, wherein the user device is configured to communicate with the medical device to facilitate medical device operation. The method may also include testing, prior to the providing the first medical application to a regulatory authority, the first medical application for compliance with one or more statutory or regulatory requirements.

The method may further include providing the certified first medical application to an online applications store.

The method may further include receiving, from a second medical application developer, a second medical application, wherein the second medical application is configured to operate a second specific medical device subject to a regulatory certification; storing, in a computer system, the second medical application; providing the second medical application to a regulatory authority for certification of the second medical application in conjunction with the second specific medical device; receiving, from the regulatory authority, a certified version of the second medical application; and providing the certified version of the second medical application to a second user device via an electronic communications interface, wherein the second user device is configured to communicate with the second medical device to facilitate medical device operation.

The medical device may be an infusion pump, a pacemaker, a defibrillator, a heart monitor, a heart control device, a blood glucose monitor, a continuous blood glucose monitor, a pulse sensor, an oxygen saturation sensor or another medical device as described herein or known or developed in the art.

The device may include data defining a collection of reference information associated with a monitoring function, wherein the medical device is further configured to provide the data to a second medical device.

Another embodiment may include a medical device, comprising: a medical monitoring or control apparatus disposed to monitor or control a patient medical function; a network communication interface; one or more processors configured to be coupled to the network communication interface and the medical monitoring or control apparatus; and a memory coupled to the one or more processors, said memory configured to include: an unsecured segment; and a secure segment logically separated from the unsecured segment, wherein the secured segment is configured to securely store a certified medical application disposed for execution on the processor to facilitate control and/or monitoring of the medical monitoring or control apparatus.

The secure segment may be further configured to securely store a set of data provided from the medical monitoring or control apparatus. The memory may further include a secure communication application configured to receive, from a service platform, a certified medical application and store the certified medical application in the secure segment. The secure communication application may be further configured to verify, in response to receipt of the medical application, that the received certified medical application has been approved for operation with the medical device by a regulatory authority. The regulatory authority may be the FDA and the certified medical application may be certified by the FDA.

The device may include two processor cores wherein a first of the two processor cores is coupled to the unsecure segment and the second of the two processor cores is coupled to the secure segment. The first processor core and the second processor core may be isolated from each other.

Some embodiments of the invention may leverage advances in technology in order to overcome barriers (e.g., shortcomings related to power consumption) mentioned in the Background section, as well as other barriers such as regulatory and statutory compliance requirements, security, quality assurance, high reliability/low probability of device error or failure as well as user and patient privacy. Such advances may include use of lower power RF technologies such as Bluetooth Low Energy and NFC, security features that create secure zones for protecting critical features of user devices (e.g., the RF link associated with wireless networks), as well as other similar or equivalent features.

In some embodiments, the security features may be especially important as user devices become a greater target for malicious activity. These security features include utilizing TrustZone by ARM, virtualization techniques and or highly reliable Real-Time Operating Systems (RTOS) by Open Kernel Labs (such as but not limited to OKL4), VirtualLogics, Green Hills Software, Wind River, etc. The advances in technology may also be utilized to increase functionality without dramatically increasing materials, cost, size and/or power requirements.

As described below, some embodiments of the invention enable user devices (e.g., mobile devices such as cellphones and PDAs, netbooks, laptops, computer devices or other similar devices) with some or all of the operational functions of a medical controller or other medical device. As used herein, a medical controller or medical device denotes a device that can be used in proximity to, in contact with and/or implanted in a patient to provide a medical function and exchange associated data. Examples include devices such as medical infusion pumps, physiological monitoring devices, heart controllers such as pacemakers and the like, as well as other similar or equivalent devices known or developed in the art for medical diagnosis, monitoring, medication or other substance delivery, electrical or other physiological control or other medical applications. A characteristic of these devices is that they are typically custom designed for a particular application or applications and are subject to regulatory review such as by the United States FDA or other regulatory authorities. In many cases, regulatory approval includes strict constraints on hardware and software used in the devices, which creates limitations as to how device software version control and testing must be done, as well as how application can be incorporated or embedded in the medical devices or otherwise provided to them.

In accordance with one aspect of the present invention, by providing access to and control of medical devices using more commonly available user devices, patients/users are provided with convenience (as many people already own or have access to user devices), choice (as there is a large variety of user devices to choose from around the world), affordability (as user devices are produced in volumes that are orders of magnitude greater than existing medical devices and controllers), and discretion (as it would be difficult to impossible for a passerby to determine if someone was managing their disease or text messaging, for example). Because of reliability standards imposed on medical devices as well as quality and version control and required regulatory testing approvals, embodiments of the invention may also provide a secure environment in a controlled fashion so as to comply with regulatory and/or statutory requirements (such as, for example, U.S. Food and Drug Administration (FDA) requirements, equivalent foreign governmental requirements, statutory requirements such as those imposed under HIPAA, or other similar or equivalent requirements) within a user device so the user device can run a software application that controls a medical device while still maintaining regulatory and/or statutory compliance, even when the non-secure environment is evolving, such as with operating system updated, firmware updated, application additions and updates, and the like, as well as store, and optionally encrypt, a user's medical information in a secure environment.

As one example of potential security advantages of embodiments of the present invention, it is important to recognize that existing user devices do not offer a secure and reliable solution that provides an alternative to posting Personal Health Record (PHR) data on one or more PHR servers, for example. As used herein, a PHR is any record, including but not limited to Electronic Medical Records (EMR), that contains health information which may or may not be interpreted as personal and sensitive. A PHR is valuable only if information in the record is current and accurate. Some users do not trust the security of online PHR services, which may be caused by well-publicized breaches of such data. However, some embodiments of the invention allow a user to store his or her PHR on a user device in a physically-present, secure, reliable and encrypted, such as but not limited to RSA cryptography, manner that ensures uncompromised integrity of the data. Having a physically-present PHR allows the user to share his or her PHR information on-demand, give the user the option to post, via a secure manner such as but not limited to Secure Socket Layer (SSL), all or only the data they want to post in his or her Server PHR, and enable synchronization of PHR data between the user device and PHR Server.

Embodiments of the present invention may include, among other things, processes and systems for managing, controlling and monitoring medical devices via a software application functioning in a secure environment. In particular, but not by way of limitation, aspects of the invention pertain to one or more networks for delivering an approved software application to a user device, the software application enabling the user device to exchange information with a medical device that is near, carried, worn or implanted in a biological environment (e.g., a human body).

Some embodiments of the present invention relate to a secure system for delivery of medical applications to a user device and/or a medical device. The secure system may further be used to manage approved medical applications and may further be used by developers of medical applications to act as an escrow or trusted third party service. In this case, a medical application developer may submit a medical application to the trusted third party service electronically or via tangible storage media, with the trusted third party service then providing the medical application to an appropriate regulatory authority, such as the FDA, for approval, and then may further manage storage of the approved application and/or delivery of the approved medical application to a user device and/or medical device.

Some embodiments of the invention may be implemented in the form of computer-executable instructions, such as program modules, being executed by a computing device, server, user device or medical device. Generally, program modules include routines, programs, objects, components, data structures, drivers, Application Programming Interfaces (APIs), an operating environment or Operating System (OS), possibly a physically secure environment (e.g. TrustZone, secure element such as but not limited to a Secure SIM, Secure micro SD, etc.) and or a virtualized environment (e.g. OKL4) which may or may not host one or more Operating Systems and/or allow applications, such as but not limited to those based on C, C++, Java, BREW, Android, Linux, Apple, RIM, Symbian, HTML and or versions of any of them, to run directly within or on top of a physically secure environment and or a virtualization layer, and the like that perform particular tasks or implement particular abstract data types.

Embodiments of the invention may be practiced in single (such as but not limited to 6xxx series chipsets from Qualcomm) or multi-core processor environments (such as but not limited to 8xxx series chipsets from Qualcomm) Embodiments may also be practiced on various processor core technologies, such as but not limited to ARM, x86, etc. Embodiments may also be practiced in environments with distributed processors, where for example one or more processors process all, some or none of the invention, and one or more additional processors process the remainder of the invention. Embodiments may also be practiced in distributed computing environments where tasks are performed by remote processing devices or services that are linked through a communications network. In a distributed computing environment, program modules may be located in both local and or remote computer storage media including but not limited to memory storage devices, servers, clouds (for cloud computing) and the like.

Attention is now directed to FIG. 1, which depicts an embodiment of a network 100 for managing and monitoring medical and user devices and delivery of medical application to such devices in accordance with the present invention. As shown, FIG. 1 includes a user device 110, a medical device 120 and a service platform 130. As those skilled in the art will appreciate, various intermediary network routing and other elements between the user device 110 and the devices depicted in FIG. 1 have been omitted for the sake of simplicity, however, would be included by those of ordinary skill in the art in various implementations. Such intermediary elements may include, for example, wireless and/or wired network devices, gateways or other server devices, and other network infrastructure provided by Mobile Network Operators (MNO) and Internet service providers (ISP).

The user device 110 is configured with hardware and/or software (shown in successive figures) that implement various medical applications as further described below in conjunction with the medical device 120. The user device 110 may include any of a variety of devices capable of operation in association with user interaction. In certain embodiments, the user device 110 includes mobile devices (e.g., personal digital assistants (PDAs), cell phones, other hand-held devices and the like), netbooks, laptops or personal computers.

The medical device 120 is configured with hardware and/or software (not shown) that implement various applications as further described below. In particular, the medical device 120 is configured to communicate with the user device 110 and/or the service platform 130, which control and/or monitor the medical device 120.

The service platform 130 is configured to send/receive data to/from the user device 110, the medical device 120 and other devices (not shown but described below), via a wireless or wired communication sub-network (not shown). The service platform 130 may be further configured to provide the medical applications to the user device 110 and/or the medical device 120, in a secure and/or configuration controlled fashion, via the communication sub-network.

Figure 2A:
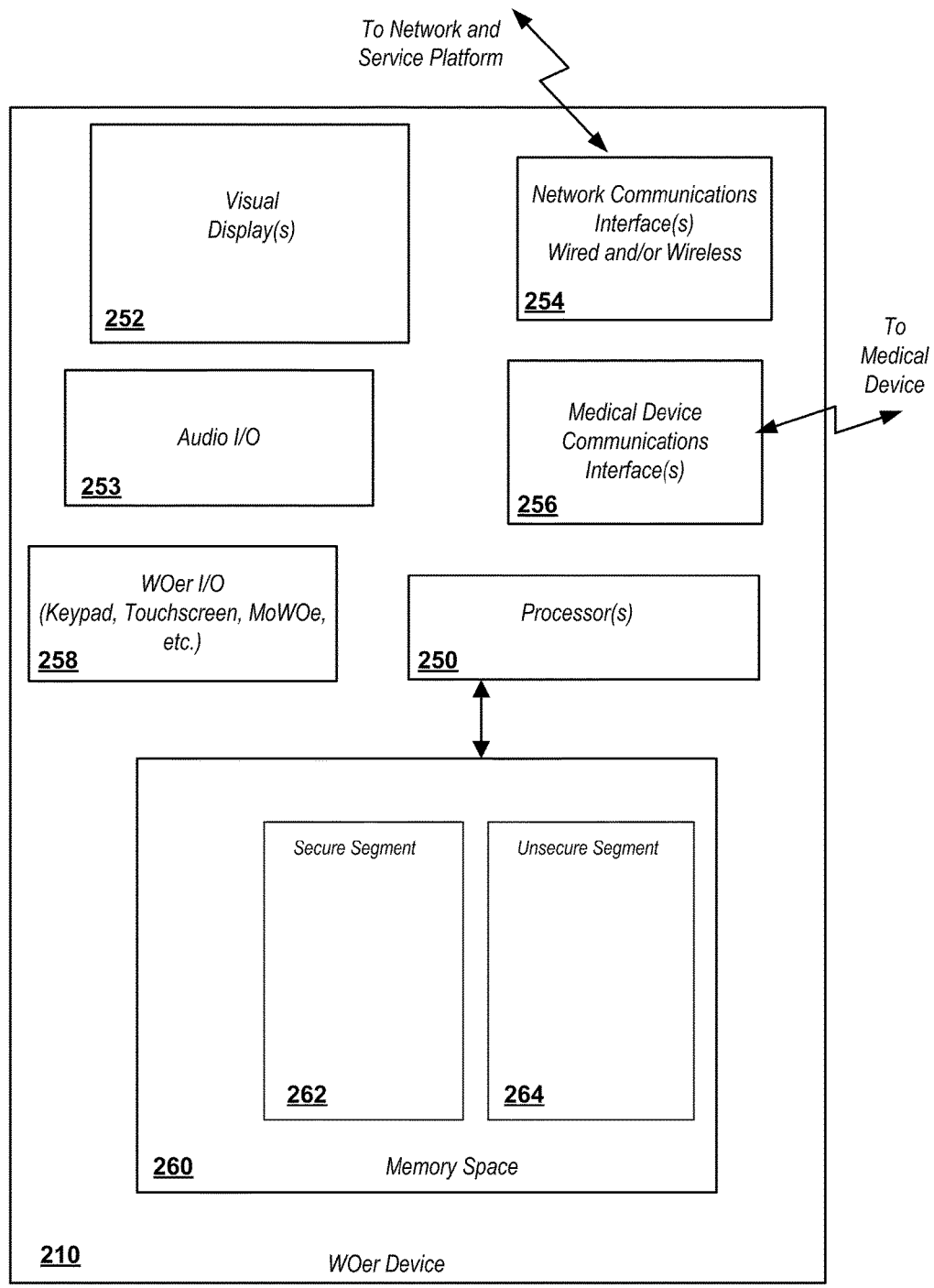
FIG. 2A depicts an embodiment of a network 200 for managing and monitoring medical devices via a software application functioning in a secure environment in accordance with aspects of the invention.

Attention is now directed to FIG. 2A, which illustrates one embodiment of an exemplary user device 210, in this case a mobile or cellular phone, which may correspond with user device 110 of FIG. 1. It will be apparent that certain details and features of the user device 210 have been omitted for clarity, however, in various implementations, various additional features of a mobile device as are known will be included. User device 210 includes one or more visual displays 252, one or more network or wireless interfaces 252 configured to provide a communications connection with a network such as the cellular network, the Internet and/or other local or wide area networks. In addition, user device 210 includes a user I/O interface 258 that may include a keypad, touchscreen, mouse or other user interface element configured to allow a user to interact with the user device 210 and with one or more applications executing on the user device 210, including medical applications. In addition, user device 210 includes a medical device communications interface 256 configured to provide a communications connection to one or more medical devices. Interface 256 may comprise a wired or wireless interface, such as USB, Bluetooth, 802.11, ZigBee and/or other similar or equivalent interfaces.

User device 210 further includes one or more processors 250, which are communicatively coupled to a memory space 260. Memory space 260 may comprise one or more physical memory devices such as SRAM, DRAM, Flash, hard drives or other memory devices. Memory space 260 is further divided into a secure segment 262 and an unsecure segment 264, each of which may store operating system (OS) code, application code and/or data. In some implementations, a single processor 260 may be coupled with both the secure and unsecure segments, whereas in other implementations two or more processors or processor cores may be respectively coupled to either the secure segment or unsecure segment so as to facilitate further segregation of the secure memory segment from the unsecured memory segment. The unsecure segment 264 may be used to store standard or typical applications such as those commonly available for smart phones, as well as associated data and operating systems for the user device. The secure segment 262 may be used to store secure applications, such as medical applications as described herein, as well as associated data. Separate operating systems may be separately stored in and used by applications operating in the secure segment versus the unsecure segment. In some embodiments, the secure segment may be provided with guaranteed processor and memory resources, which may be done to protect against attacks on the device such as denial of service attacks or other ways of attempting to overload processing and/or memory usage.

Figure 2B:
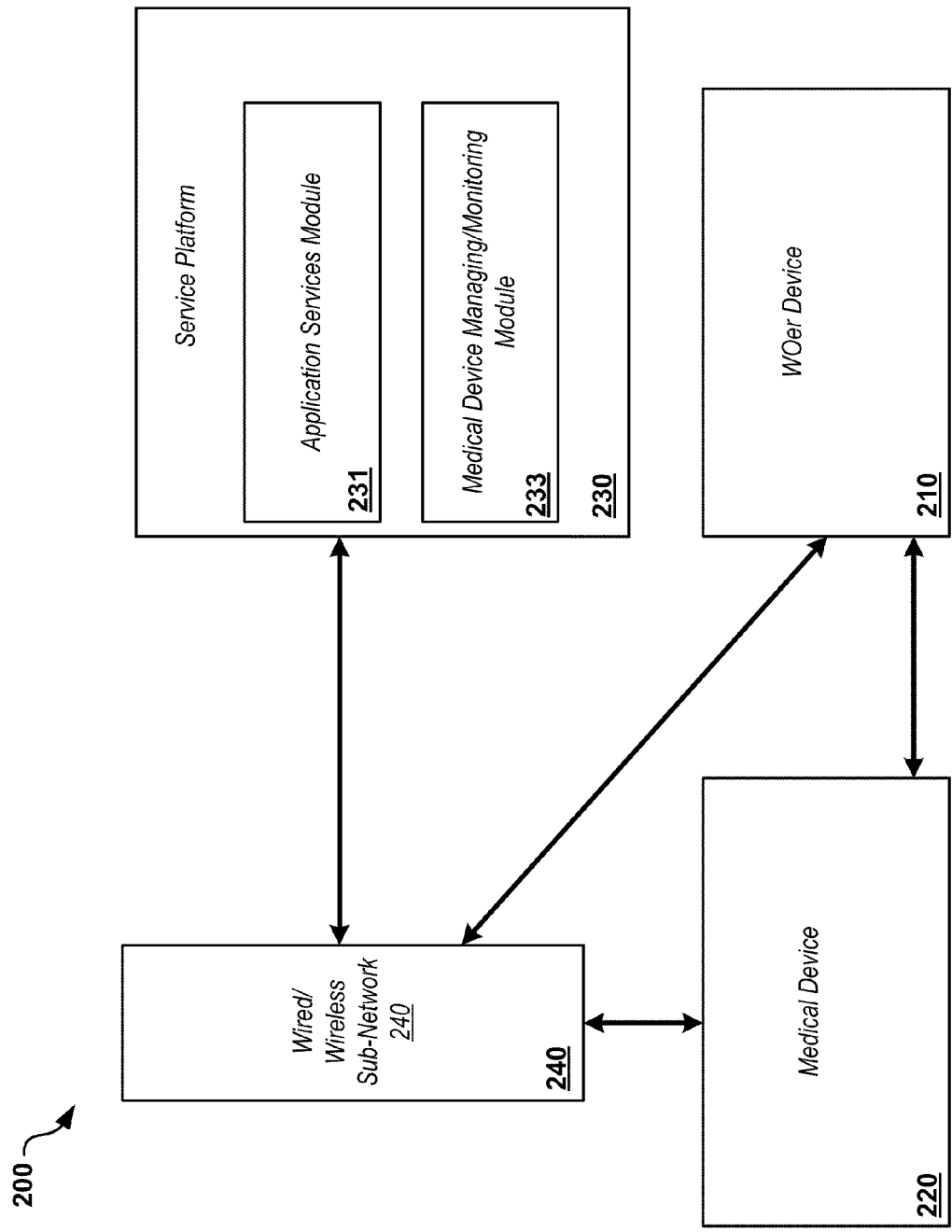
FIG. 2B depicts an embodiment of an exemplary user device in accordance with aspects of the present invention.

Attention is now directed to FIG. 2B, which illustrates additional details of embodiments of a user device 210 and associated network, which may correspond with user device 110. While details of various embodiments of the invention may vary and still be within the scope of the claimed invention, FIG. 2B shows a block diagram depicting a typical network 200 for managing and monitoring medical devices in accordance with at least one embodiment of the present invention. The network 200 is only one example of a suitable environment and is not intended to suggest any limitation as to the scope of use or functionality of the invention.

As is shown in FIG. 2B, the network 200 includes a wired/wireless communication sub-network 240 that enables communications among the user device 210, the medical device 220 and the service platform 230.

In accordance with communication between the user device 210 and the service platform 230, the communication sub-network 240 may include network infrastructure and communication pathways provided by MNOs and/or Mobile Virtual Network Operators (e.g., when the user device 210 is a mobile device) or ISPs (when the user device 210 is a laptop or personal computer). One of skill in the art will appreciate alternative configurations associated with the communication sub-network 240 that are within the scope and spirit of the invention, including such configurations that make use of wireless transport technologies (e.g., CDMA, GSM/GPRS, EDGE, WCDMA, WiFi, WiMAX, HSxPA, LTE, etc) and other communication services (e.g., Internet Protocol Suite (IPS), Hypertext Transfer Protocol (HTTP), Secure Socket Layer (SSL), etc).

In accordance with communication between the user device 210 and the medical device 220, the communication sub-network 240 may include wired or wireless technologies such as, for example, Bluetooth, Bluetooth Low Energy, ANT, MICS, MEDS, NFC, RFID, Zigbee, WiFi, WiMAX, CDMA, UMTS, LTE, spread spectrum frequency hopping, paging, USB, Firewire, proprietary, etc.

In some embodiments, communication among the user device 210, medical device 220 and service platform may utilize security technologies such as encryption/decryption (in an exemplary embodiment 128-bit encryption or higher), cryptography (including but not limited to that used in RSA encryption), Internet Protocol Security (IPSec), Secure Socket Layer (SSL), Virtual Private Networks (VPN), firewalls and data management zones, demilitarized zones (DMZ), cloud computing and the like. Additional embedded security technologies include those built into Bluetooth, Bluetooth Low Energy, NFC, HTTPS, and token-based security (e.g., challenge questions, passwords, private/public keys, static or rolling algorithms) and the like. For example, rolling algorithms may be utilized in relation to communication between the user device 210 and the medical device 220. In such an embodiment, medical device information (e.g., Pacemaker information) may be transferred using a custom tailored algorithm of "divide the data by decimal 10." During a subsequent transfer of information, a custom algorithm of "multiply the data by 2 and take the square root" may be used as two high-level dynamic yet simplistic examples. The custom algorithms can (and should) be updated frequently.

FIG. 2B also depicts a service platform 230 that includes an application services module 231 and a medical device managing/monitoring module 233 (e.g., each running on an application server (not shown)). The application services module 231 operates to safely receive, maintain and distribute medical applications that are used by the user device 210 to manage/monitor the medical device 220, for example. Each of the functions related to the application services module 231 are described in more detail below. The medical device managing/monitoring module 233 operates to receive/send data from/to various devices in the network 200 in accordance with managing or monitoring a medical device 220. Details of implementations of each of these functions are described further below.

Certain aspects of the network 200 may require approval, oversight and/or certification by the Food and Drug Administration (FDA) or other medical and/or government or industry regulatory authorities. For example, modules 231 and 233 may require approval, oversight and/or certification by a medical authority to guarantee the integrity of the medical applications (e.g., before the service platform 230 grants permission to download the applications to the user device 210), and also to ensure the secure collection and distribution of the medical information provided by the medical device 220. The user device 210 may also (or alternatively) require approval, oversight and/or certification by a medical authority to guarantee the integrity of the operation of the medical applications (e.g., after the service platform 230 downloads the applications to the user device 210), and also to ensure the secure collection and distribution of the medical information provided by the medical device 220. Embodiments of the present invention may facilitate compliance with these requirements, as well as other statutory or regulatory requirements.

One of skill in the art will appreciate that the need for government-based or industry-based regulation on a complete, one-off system may be overcome or at least improved by adoption of a scalable industry standard, which may be in accordance with the disclosure described herein. Such an industry standard may be adopted by manufacturers, vendors and providers of the user device 210, the medical device 220 and service platform 230, and the operations thereof. One of skill in the art will also appreciate that, in accordance with some embodiments, there may be no need for any regulation at all (e.g., government-based or commerce-based).

The user device 210 may be configured to serve as a slave, master or a combination slave/master to the medical device 220. In accordance with one embodiment, the medical device 220 may host and run some or all of a medical application (e.g., run a preinstalled application installed from the factory for example, and/or a downloaded application to the medical device 220 from the service platform via the user device 210 acting as a gateway). In such an embodiment, the medical device 220 may only request/allow the user device 210 to respond to requests from the medical device 220 that require user intervention, and or to act as a gateway though which data from the medical device 220 passes to service platform 230. In order to do this, application space and/or data memory space in the user device 210 may be securely partitioned to insure security, privacy, reliability, quality and/or regulatory compliance.

In some embodiments, the medical device 220 may only run the lowest level logic necessary to make the medical device 220 perform its most fundamental purpose(s). Under such an embodiment, higher-level instruction may be managed and provided by the user device 210. In order to do this, application space and/or data memory space in the user device 210 may be securely partitioned to insure security, privacy, reliability, quality and/or regulatory compliance. One of skill in the art will appreciate other embodiments regarding the interaction between a medical device 220 and the user device 210 that are within the scope and spirit of the invention.

In accordance with one embodiment, the service platform 230 is configured as a slave, master or a combination slave/master to the medical device 220 and/or medical device 210. Under this embodiment, an authorized medical agent (e.g., a physician, nurse, etc) may, using a computing device that may or may not be mobile, communicate with the medical device 230 via the user device 210 and/or the service platform 230. For example, the service platform 230 could allow a nurse to remotely update the settings of the medical device 220 through a webpage, cloud or back office software that has been integrated into the service platform 230. In an alternative embodiment, the settings could be updated automatically based on a pre-programmed software package that is compatible with the needs of the user/patient's medical device 220. These embodiments each offer the advantage of eliminating a need for the medical agent to be physically near the medical device 220 in order to update its settings. In order to do this, some elements of the service platform 230 may be configured with secured application and/or data storage space/memory so at to guarantee privacy, ensure regulatory compliance, manage application integrity and/or provide other security, quality or reliability features.

With appropriate authorization levels, individuals such as users/patients, doctors, nurses, parents, guardians, etc, could be granted access to the managing/monitoring functions associated with the medical device 220 through the service platform 230. The type of access may be restricted to receiving certain information, or may provide for full remote control of the medical device 220. For example, a user/patient in Haiti may only be allowed access to view the usage history of the medical device 220, while a physician who is located in the United States may be allowed the capability of remotely update settings to the medical device 220.

In other embodiments, the user device 210 is configured as a gateway that merely passes data to/from each of the medical device 220 and the service platform 230. In accordance with this embodiment, the user device 230 can open up an appropriate communication pathway (e.g., an RF pathway) to communicate with the medical device 220 and the service platform 230. The user device 210 may alternatively be configured as secure middleware that stores data transmitting between the medical device 220 and the service platform 230. Such a configuration has the advantage of preserving data in case the connection between the medical device 220 and the service platform 230 becomes suspended. In order to do this, application space and/or data memory space in the user device 210 may be securely partitioned to insure security, privacy, reliability, quality and/or regulatory compliance.

The user device 210 can alternatively be configured to act as the device responsible for ensuring that data was completely and correctly transferred to/from the medical device 220 and service platform 230. The user device 210 may be further configured to provide updates to each of the medical device 220 and the service platform 230 as to the status of a transmission. The user device 210 may accept all of the transferred information from either the medical device 220 or service platform 230 before transmitting part or all of it to the service platform 230 or medical device 220, respectively. In order to do this, application space and/or data memory space in the user device 210 may be securely partitioned to insure security, privacy, reliability, quality and/or regulatory compliance.

In accordance with yet another embodiment, the user device 210 is configured to receive user-inputted health information regardless of whether the user has a medical device 220. Such health information may include nutrition facts, medication information such as but not limited to compliance, Personal Health Record (PHR) information, etc. The user device 210 may then provide a secure and reliable environment (discussed below) for such information. This embodiment provides a viable alternative for people that don't feel comfortable uploading part or all such information to the World Wide Web, yet still provides such individuals with a readily available and secure access to the information. This embodiment may also provides a localized backup for server-based PHR data in case something should happen to the data stored in server-based solutions (e.g., Google Health and Microsoft Vault). Synchronization between the user device 210 and an online database or a medical agent's computer is also possible via fixed and/or variable parameters (e.g. frequency of synchronizations, specific fields to sync/not sync, which remote databases to/not to sync with, etc.).

Medical Applications

As described herein, Medical Applications are software-based solutions for managing, monitoring and/or controlling a medical device, such as devices 120 and 220 shown in FIGS. 1 and 2 respectively. A medical application or applications may run on various components in the network 200, either in its entirety or in a distributed fashion, including on the user device 210 and the medical device 220. In some embodiments, the medical applications run on a computing device (not shown) operated by a third-party (e.g., a medical agent such as a doctor, nurse or other medical care provider). In other embodiments, the medical application runs on the service platform 230, which is accessible to authorized individuals, such as medical agents via the communication sub-network 240 (e.g., based on a web-based solution).

Medical applications may be developed by application developers, manufacturers of the user device 210 and/or medical device 220, or any other suitable entity. Various embodiments for developing and approving medical applications in accordance with aspects of the present invention are described below with respect to FIG. 7. In particular, a medical application may be developed by a third party application developer, managed by a trusted third party service provider associated with the service platform, who may control and/or manage regulatory approval of the application with a regulatory provider such as the FDA, as well as control provision of the application, in a secured, reliable and/or regulatorily compliant fashion, to the user device 210.

In some embodiments, medical applications may be downloaded directly from the service platform 230 via the communication sub-network 240. In accordance with one embodiment, medical applications are downloaded from the service platform 230 to the user device 210 without any alteration to the medical applications on the user device 210. That is, the medical application that leaves the service platform 230 is the same medical application that operates on the user device 210. This may be done in a secure fashion so as to ensure reliability, integrity and/or quality of the downloaded application. The user device 210 may include additional applications or other forms of executable programs to determine whether the downloaded medical application is appropriate for execution on the user device and/or is compliant with required regulatory and/or statutory requirements.

The service platform 230 and user device 210 may also be configured to confirm that a medical application was downloaded successfully prior to installing or executing the medical application. If the medical application did not download or install successfully, part or all of the medical application may be removed from the user device 210, and the user and the service platform 230 may be notified so as to analyze any problems associated with the download or install. The service platform 230 may also then forward such notifications, with, in some cases, additional detail (e.g., the time, date, user device make and model, medical application version, etc.) to additional parties, such as the developer of the medical application, trusted third parties, other quality assurance entities and/or regulatory authorities, for example.

A download may consist of an entire medical application (e.g., a new or replacement/upgrade), or it may be a sub-application for an existing application (e.g., an upgrade perhaps with new features or a patch for example).

In an exemplary embodiment, a user device 210 includes a secure environment, which may include a secure application operating environment, secure data storage environment, secure and/or separate OS, or combinations of these elements. The secure environment may be stored in a secure segment of a user device memory space, such as secure segment 262 as shown in FIG. 2A. In some embodiments, a medical application is downloaded to a secure environment on the recipient device (e.g., the user device 210). In addition, data associated with the medical application may be stored in the secured environment. Additional details of certain exemplary embodiments relating to secure environments are discussed in greater detail with respect to FIG. 3 (e.g., secure environment 311).

When downloading to the secure environment, it is possible that the medical application never passes through the operating system (OS) and/or memory of a non-secure environment, though it may be possible in some embodiments. Certain embodiments relating to non-secure environments are discussed in greater detail with respect to FIG. 3 (see non-secure environment 313).

Figure 3:
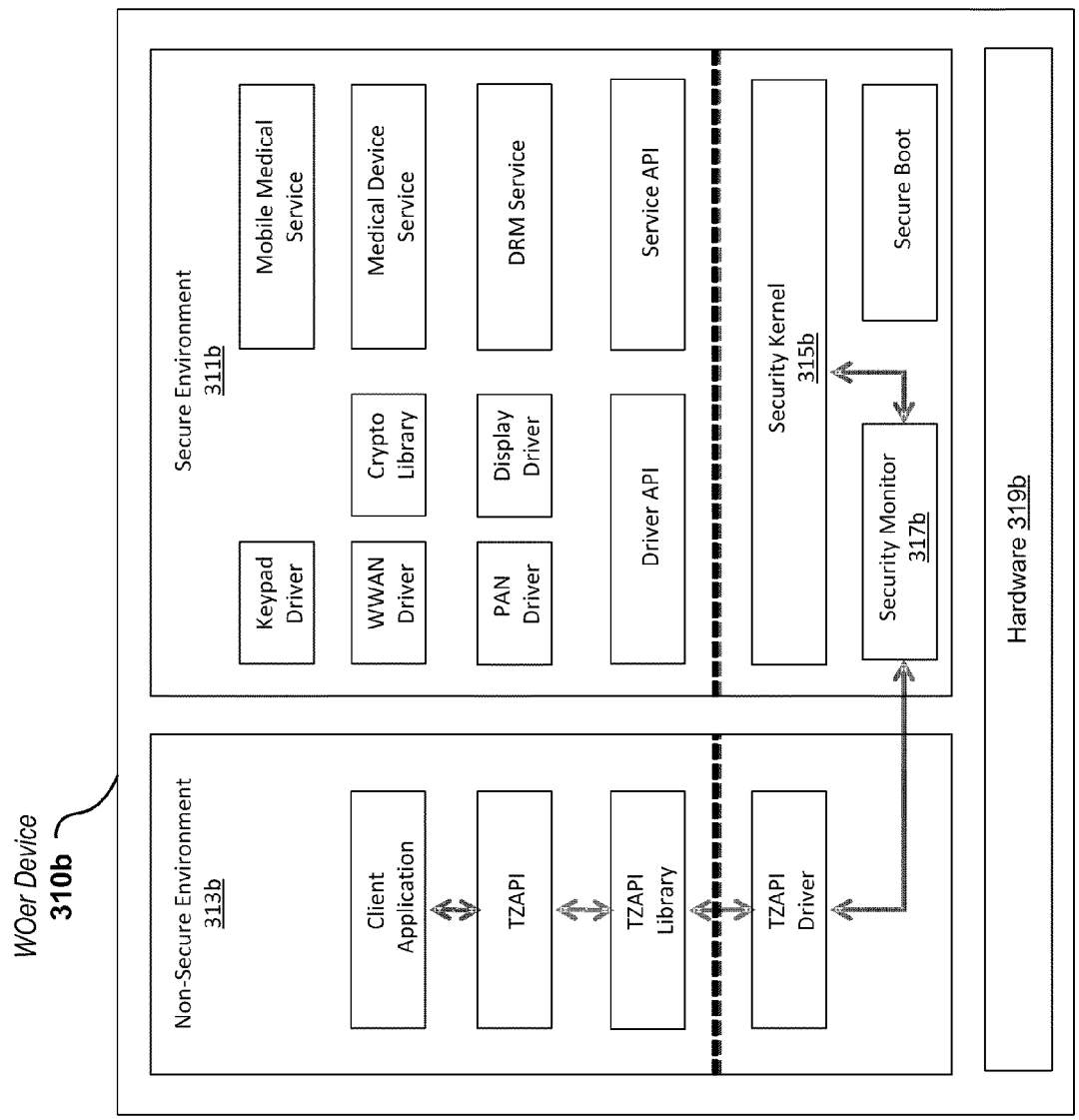
FIG. 3 depicts embodiments of alternative hardware and software architectures that may be implemented in relation to a user device in accordance with aspects of the invention.
Figure 3:
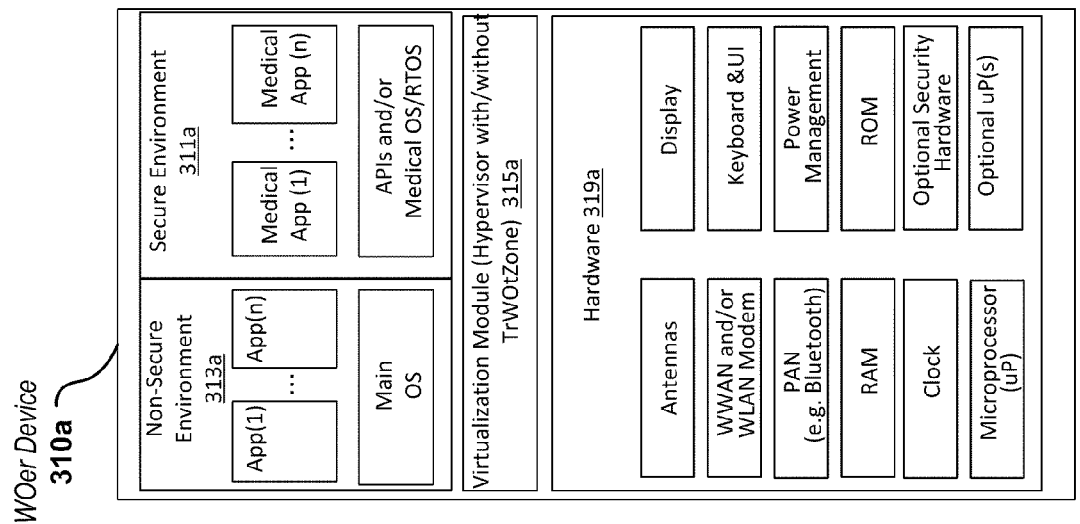

Selection of a medical application may occur via a web browsing function on the user device 210, a remote device, or any other suitable method. The same methods for securely operating a medical application on a user device 210 are available when downloading the medical application. Additional details are shown in FIG. 3 and further described below.

In some embodiments, medical applications may run within secure and/or non-secure environments (e.g. physically secure element and/or virtualized environment, for example). However, in accordance with an exemplary embodiment, all of a medical application resides within a secure environment. In alternative embodiments, a medical application may reside outside of the secure environment, either completely or partially. Under circumstances when the medical application partially resides outside of the secure environment, some form of a pointer/interrupt may be used to call critical aspects of the medical application that reside within the secure environment. Such critical aspects may include changing settings within the medical device.

Medical applications on the user device 210 are generally intended to perform at least the same or similar services that applications on medical controllers perform. As one example associated with a diabetic patient, instead of the patient carrying around Insulet's OmniPod controller device to deliver a bolus or change their basal rate, the patient would be provided with an interface to open an equivalent medical application on their user device 210 (e.g., a mobile device) and perform the same functions without need for the controller. However, it is apparent that ensuring the quality, reliability and security of the equivalent medical application while operating on the user device 210, rather than the dedicated controller, is typically important.

User Devices

Attention is now directed to FIG. 3, which depicts embodiments of hardware and software architectures in relation to an embodiment of a user device 310a and another embodiment of a user device 310b (collectively referred to herein as "user device 310"). The user device 310 is configured to receive/transmit data from/to a medical device (e.g., medical device 220) and a service platform (e.g., service platform 230). Though not required, the user device 310 may offer one or more services that include voice communications (e.g., cellular, Voice Over IP, etc), SMS/text messaging, email, calendar, camera, video, music, social networking, internet and intranet browsing, location-based services (LBS), application shopping and the like.

The user device 310 may include a secure environment 311 (the collective notation for secure environments 311a and 311b) and/or a non-secure environment 313 (the collective notation for non-secure environments 313a and 313b). These secure environments may include memory segments 262 and 264 of FIG. 2A and may include one processor 250 or two or more processors 250a, 250b . . . 250n (not shown). At a high-level, this architecture allows for the safe and secure coexistence of healthcare applications (in the secure environment 311) that may or may not require oversight from regulation agencies such as but not limited to the FDA, and consumer-centric applications (in the non-secure environment (313) such as but not limited to phone, calendar, email, internet browsing, social networking, VoIP, SMS and MMS, location based services, mobile banking, etc. This architecture also allows medical device companies to use software and tools that they may be more familiar with and or confident in within a secure environment 311, while also protecting their proprietary knowledge from the benefits of open platforms (e.g. Linux, Android, etc.) for example, as well as platform challenges and risks.

Secure environment 311 may be configured to provide a secure, reliable and separate operating environment for medical applications that are used to manage/monitor a medical device (not shown). The secure environment 311 is configured to be as thin as possible in relation to managing tasks. For example, the secure environment 311 manages the downloading and running of medical applications, which may or may not include Digital Rights Management (DRM) as is used to permit the playback of downloaded and paid for multimedia files on mobile devices for example, or similar techniques, without having to manage many additional tasks. In order to perform these tasks, the secure environment 311 may require access to a user interface (UI) that includes items such as a keyboard, roller ball, buttons, screen, touch screen, RF components, processor, memory, etc). The secure environment 311 may be configured to be OS agnostic, which allows any code to quickly be ported to other devices that support the secure environment 311.

For illustration purposes, a mainstream operating system (main OS) is shown only in the non-secure environment 313a. The main OS manages and coordinates activities and the sharing of the limited resources of the user device 310a. One of skill in the art will appreciate an arrangement in the user device 310b that includes a similar main OS to that shown in the non-secure environment 313a. One of skill in the art will further appreciate that multiple Main OS's (e.g., Android, Apple, BREW, Java, Linux, RIM, Symbian, Windows CE, Windows Mobile, etc.) may be deployed. Alternatives to the main OS include a Real Time Operating System (RTOS) and/or native Application Programming Interfaces (API). Optionally, a mainstream operating system as described above may also serve as a Medical OS or RTOS in the secure environment 311a. The medical OS or RTOS may not necessarily be a true OS or RTOS, but instead any environment that allows applications to run, and/or requisite drivers, etc. to be referenced (e.g. an area that allows C, Java, HTML, etc to run for example). HTML for example is beneficial due to the broad developer base. In one embodiment, the secure environment 311 would be able to reference one or more HTML-based webpages which are maintaining the latest application in HTML format; the secure environment 311 would simply cache the webpage and run it or a version of it as the application in an existing or new cell.

Attention is now directed to the user device 310a, which is configured using a shared-hardware architecture (also referred to as a "virtualization" configuration). The shared-hardware architecture may be configured with a single or multi core processor, one or more memory components, one or more Bluetooth and/or NFC radio components for communicating with the medical device 220, one or more radio components (e.g. RFID, Zigbee, WiFi, WiMAX, CDMA, UMTS, LTE, etc.) for communicating with the Service Platform 230, serial and/or USB communication components, display, antennas, battery, power management, external memory components, headphone jack, microphone, speakers, etc., any of which may be shared by the operations of the secure environment 311a (e.g., running medical applications (described below)) and/or the non-secure environment 313a (e.g., running mainstream applications (e.g., carrying-out voice calls, email, calendar, Bluetooth headset, internet, social networking, etc)).

The virtualization feature 315a is configured to make elements above the hardware 319a, e.g., the OS and various applications, operate as if those elements are running directly on top of the hardware 319a. Moreover, these elements may further operate as if they are exclusively on the hardware 319a. The virtualization feature 315a allows one or more environments (e.g., the secure environment 311a, the non-secure environment 313a) to share the hardware 319a. For example, two or more separate operating systems (e.g., Windows Mobile and Linux) could be running on the same device, and perhaps without even knowing that the other operating system is present. One or more medical applications may run in serial (by itself) or parallel (alongside other secure or unsecure applications) in the Secure Environment 311a. One or more Secure Environments 311a may run in serial or parallel in the User Device 310a. on one or more Attention is now directed to the user device 310b, which is configured with a dedicated-hardware architecture (also referred to as a "security kernel" configuration). A dedicated-hardware architecture may be configured with single or separate physical processors, memories, peripherals, etc, that are each dedicated to the operation of the secure environment 311b (e.g., running medical applications) or the operation of the non-secure environment 313b (e.g., running mainstream applications). For example, the dedicated-hardware architecture may utilize security kernel features that prevent unauthorized access to, or use of, the system resources used by the secure environment 311b.

By way of example, the portion of the user device 310b shown in FIG. 3 includes a security monitor 317b that sits underneath the security kernel 315b in the secure environment 311b. The security monitor 317b looks for traffic on the user device 310b that is flagged as requiring security. For example, ARM TrustZone sets the 33$^{rd}$ bit low or high depending on whether particular traffic requires security. Traffic requiring security (also referred to as secure traffic) is identified by the security monitor 317b and managed within the secure environment 311b with the security kernel 315b, processes, applications, etc. By way of example, a user may make use of a particular function (e.g., making a phone call) of the user device 310b via an application running in relation to a main OS within the non-secure environment 313b (e.g., the security monitor 317b does not recognize any requirements for secure traffic). When user attempts to make use of a particular function (e.g., via the same or different application) that requires security (e.g., controlling an internal defibrillator), the security monitor 317b identifies the security requirement, and begins to manage the application within the secure environment 311b. The application may be managed within the secure environment 311 using any sort of secure code (e.g., native secure code that has been approved by a medical authority like the FDA). After the particular function is carried out, the security monitor 317b will determine if any additional functions require security (e.g., must be carried out in the secure environment 311b). If there are no such functions that require security, the security monitor 317b allows the application to run in the non-secure environment 313b.

In accordance with certain embodiments, the secure environment 311 uses one or more technologies that enhance security, including virtualization (e.g., a hypervisor), Real Time Operating Systems (RTOS), virtual memory and/or virtual machine management (VMM). Technologies that enhance security may be provided via any viable source, including those technologies provided by Open Kernel Labs, Green Hills Software, VirtualLogics, Wind River, ARM (TrustZone), etc.

One of skill in the art will appreciate hybrid architectures (shared and dedicated hardware architectures) that allow for the operation of the secure environment 311 (e.g., running medical applications) on hardware dedicated to the purpose of running medical applications, and hardware that is shared by the operations of the secure environment 311 and the non-secure environment 313.

In accordance with one embodiment of the present invention, the user device 310 must provide a reliable, separate and secure (either physically or virtually) operating environment for medical applications that perform various functions (discussed below). This can be accomplished by guaranteeing processor and memory allocation, master bus control, and/or other techniques to the secure environment 311. The user device 310 may also be configured to boot directly and securely into the secure environment 311 (e.g., into a secure OS) instead of booting into a main OS. This design bypasses possible breach attempts from the main OS. In addition, the design enables the secure environment 311 to run even when the main OS becomes corrupted, needs to restart, is turned off for any reason (during a flight for example), etc.

Additional security features include limiting access to the functions of the secure environment 311 based on user name/password requirements and/or public/private keys. Such features protect the user information and potentially user's life (as the user device 310 can control a medical device such as an insulin pump and pacemaker for example). Additionally, the secure environment 311 may be configured to erase and wipe all or just health related data within it under certain circumstances (e.g., if a wrong password is entered a predetermined number of times, upon remote request via a service platform, etc).

The secure environment 311 may also be configured to offer rules and application programming interfaces (API) to communicate with a main OS, RTOS, etc. Examples of rules may include but are not limited to if, how and when to exchange information derived from the Secure Environment 311 to/from other Secure Environments 311, applications and/or non-Secure Environments 313, priorities (such as but not limited to what to do when delivering insulin and a low battery alert occurs and/or a phone call and/or email is received to the user device 210, etc.). Examples of such APIs may include but are not limited to setting a basal rate of insulin or initiating a bolus delivery, changing defibrillator settings, etc. Such rules and APIs would be stored in a library within the medical device 120 and/or user device 110 and/or service platform 130. Such rules and APIs introduce the opportunity to certify (with the FDA for example) this portion of lower level logic (rules and APIs) once for many users, medical device companies, mobile device manufacturers, etc. Rules and APIs may evolve (create new, edit, delete) over time. The rules may prohibit the secure environment 311 from communicating with the main OS as an example. Alternatively, the rules may provide for an Emergency Contact Triage medical application that automatically contacts authorized medical agents in a predefined order and manner under certain circumstances (e.g. if a user's Blood Glucose Level (BG) drops or is trending to a dangerous level without the user acknowledging the concern after one or more warnings from the user device 110 and/or medical device 120 and/or service platform 130).

The secure environment 311 may also be configured to authorize and grant/deny access to a secure environment operating on a medical device. This feature prohibits unauthorized devices and/or medical applications from communicating with the medical device. This configuration may be accomplished using standard and/or custom methods. Standard methods may include Bluetooth's Health Device Profile (HDP), Bluetooth's embedded security features, NFC's embedded and value-added security features from third parties, TCP/IP with IPSec and or SSL, a client on both the user device and the medical device to establish a VPN, public/private key pairs, etc. Custom methods may include fixed message length, custom algorithms as an initial, intermediary or final encryption/decryption step, rolling algorithms and/or public/private keys managed internally within the user device 310, the medical device and/or the service platform, etc.

The secure environment 311 may also be configured in accordance with an industry-standard framework (e.g., API sets) understood and used by application developers to quickly and consistently write safe, secure and reliable medical applications that interact with medical devices. For example, as Qualcomm's Binary Runtime Environment for Wireless (BREW) software development kit (SDK) offers a common API for sending an SMS text message across many user devices, the secure environment 311 may support common APIs depending on the task (e.g., a task regarding the delivery of a Bolus in relation to multiple insulin pumps from Medtronic, Abbott, and J&J).

The user device 310 may be configured to support one or more secure environments 311 and one or more medical applications within each secure environment 311. Each secure environment 311 offers each medical application the same reliable separation from other medical applications as the secure environment 311 has with other secure environments 311 and other environments of the user device 310. This will benefit medical application developers in several ways. For example, the developers can release a subset of a full-featured medical application to get the product to market (e.g., only the core functionality of delivering a bolus or changing the basal rate for a diabetic). That developer (or another developer) could subsequently release additional subsets of the full-featured medical application (e.g. a food library or pacemaker configurator for example). From a verification, validation and overall safety and security perspective, the subset of code can be reviewed and accepted faster and with greater confidence as it will reside alone, with less code to validate, in a reliably separate space from the other core medical application(s).

The secure environment 311 may offer rules for system priorities and exchanging information between medical applications. For example, one rule may state that in no circumstances may a pace maker medical application and its database interact in any way with a defibrillator medical application and its database, while another rule may allow every medical application to read/write from/to a PHR with proper authentication. A priority example may include but is not limited to how to handle email and low battery alerts while delivering a bolus for example). Proper authentication may include a public/private key exchange between the medical applications, an administrative password, encrypting the data, etc.

A PHR can store all or parts of the interactions between the user device 310, medical device and/or the service platform. For example, the PHR can augment more common PHR data such as allergies, diseases, etc, by logging items such as continuous glucose sensor information, defibrillator events and alarms, pace maker rhythm setting changes, drug delivery amounts, dates and times.

The secure environment 311 may also be configured to ensure that any installation of a medical application was successful prior to allowing the user to have access to the medical application.

As an added security measure, the secure environment 311 may be provided to user device manufacturers (e.g., semiconductor manufactures like Qualcomm, TI, Broadcom, NXP, Infineon, Marvel, etc) in an encrypted binary secure environment package with little to no tools (to further ensure its manufactured authenticity and integrity). A particular secure environment 311 initially and continuously checks the integrity of any environment and/or medical applications that try to interact with that secure environment 311.

The secure environment 311 may also be configured to act as a translator for data (e.g., communication to and/or from a medical device). For example, one medical device manufacturer may provide a "Deliver Bolus Complete" acknowledgement directly to user devices that follow a common API set, whereas another medical device manufacturer may opt to, possibly for legacy product reasons, transfer the same acknowledgement outside the approved API set. The secure environment 311 (and perhaps a medical application) may translate that information so it is understood by the user device 310, secure environment 311 and service platform. By providing this translation function, medical device manufacturers can program medical devices to grant/deny certain data and commands, as well as provide extra security and data integrity checks, all with a scalable approach to support growth for future roadmaps while providing a relatively easy approach for supporting legacy and/or proprietary product/code.

Alternatively, medical device data could be passed as an encrypted packet that is only decipherable and understood by a medical device manufacturer's medical system the Service Platform 130, and/or any service connected to the Service Platform. For example, Abbott may want to encrypt some or all of the information coming from their medical devices so such information can pass through the user device 310 via the secure environment 311 to Abbott.

In some embodiments, a user device may be configured, as described previously, to prevent attacks on processing and/or memory, such as denial of service attacks. In one implementation, a specifically defined amount of available memory may always be reserved for use in the secure memory segment so that any medical application executing from the secure segment have ample memory resources. Likewise, processor allocation may be done in a similar fashion to guarantee at least a minimum amount of processor time for the medical application.

In some embodiments, boot configuration of the user device may be configured so that an operating system or kernel associated with the secure environment and secure segment always boots first before any OS or application in the non-secure environment. In this way, "rogue" applications in the non-secure segment may be precluded from taking over system resources and the availability of the medical application can be guaranteed.

In some embodiments, additional operating modes may be provided in the user device for situations requiring shutdown of the user device. For example, some current cellular phones have a "flight" mode where the phone is partially shutdown during flight. Alternately, without this mode, the phone must be turned off entirely. When the phone is partially shut down, all of the communications links (e.g. wireless links) are turned off so that no RF signals are emitted or received. In the case of a user device configured as described herein for operating a medical application, however, the user device off may not be an option as it could impair the functionality of an associated medical device. Moreover, even a "flight" like mode may preclude operation of the medical device by turning off personal area network (PAN) connectivity, such as via Bluetooth, Zigbee, etc. Accordingly, an additional operating mode may be provided in the user device wherein WAN connectivity (i.e., cellular, LTE, etc.) is disabled, whereas PAN connectivity is enabled sufficiently to maintain connectivity between the user device and medical device. In addition, alarms or other indications may be provided to a user from the medical device and/or user device when the PAN connectivity is off and/or intermittent.

Medical Devices

Figure 4:
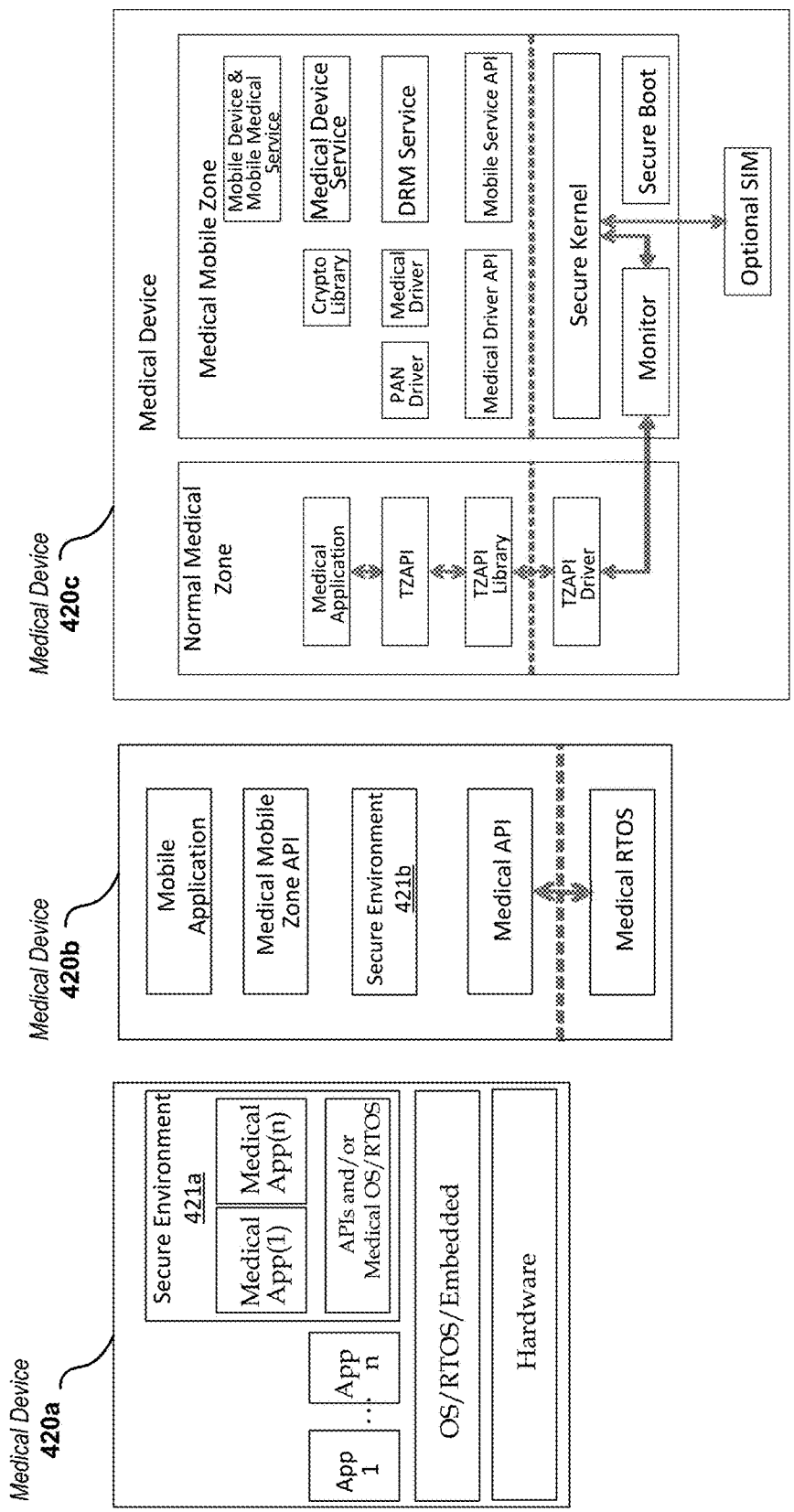
FIG. 4 depicts embodiments of alternative hardware and software architectures that may be implemented in relation to a medical device in accordance with aspects of the invention.

Attention is now directed to FIG. 4, which depicts hardware and software architectures of embodiments of medical devices 420a, 420b and 420c (collectively referred to as "medical device 420") in accordance with at various embodiments of the present invention. While referring to FIG. 4, simultaneous references may be made to FIGS. 2A, 2B and 3. The medical devices 420 can receive and transmit data to/from the user device 310 and/or the service platform 230 via the communication sub-network 240.

Medical device 420 may comprise any compatible device used in the health and wellness markets. Medical devices generally include sensor and/or control apparatus for monitoring and/or controlling physiological properties or functions such as body chemistry (blood, urine or other bodily fluids, etc.), electrical and associated physiological functions (heartbeat, blood pressure, pulse, respiration, brain or neural activity, etc) or other patient characteristics or functions, which may be done by electrical, chemical, optical, electromagnetic, contact or other sensor and associated electronic and mechanical hardware and software as are known or developed in the art. Representative examples of such devices include pace makers, blood glucose sensors, defibrillators, IV machines, drug delivery systems, heart rate sensors, wireless medication/pills, smart Band-Aids, weight scales, blood glucose monitors and continuous blood glucose monitors, pulse sensors, blood pressure sensors, oxygen saturation sensors, sleep quality sensors, EEGs, EKGs, weight sensors as well as other medical devices known or developed in the art.

Medical device 420 may utilize technologies that are discussed above with respect to the user devices 210 and 310 and may be configured to include some or all of the associated elements shown in FIGS. 2A, 2B and 3, and in particular the processor or processors and memory used in the secure environment. (In particular, see discussion related to FIG. 3, which is incorporated here by reference in relation to the medical device.) For example, the medical device 420 may include secure environments that operate to control operational aspects of the medical device 420. These secure environments may or may not be similar to the secure environment 311. The medical device 420 may also communicate with the service platform 230 via the communication sub-network 240 (e.g., UMTS, LTE, WiFi) directly or via the user device 210. The medical device 420 may even have a user interface (UI) (e.g., a screen, keypad, buttons, etc) to enable a user to manage or monitor the medical device 420.

As noted above, the medical device 420 may include a secure environment. The secure environment may be applied to dedicated, shared or hybrid hardware architectures, which also include hardware specific to the medical operation of the medical device (e.g., alarms, system checks, accelerometer reads, IO, etc).

The medical device 420 may be configured to communicate with the user device 310 to pass instructions and/or data. For example, the medical device 420 can store and later forward software and/or parameters if and when the user device 310 is showing signs of corruption or upon a user request. Data may be stored, buffered and exchanged (First In First Out (FIFO) or Last In First Out (LIFO) with the user device 310 and the service platform 230. The exchange of data may occur via the communication sub-network 240, and may or may not pass through secure environments in the medical device 420, the mobile device 310 or the service platform 230.

As an added security measure, any secure environment may be provided to medical device manufacturers (e.g., Abbott, J&J, Medtronic, etc) in an encrypted binary secure environment package with little to no tools. The secure environment initially and continuously checks the integrity of the secure environment 311 and/or medical applications that try to interact with the medical device 420.

The medical device 420 may be configured to act as a translator for data (e.g., commands from a user device). By way of example, one medical device manufacturer may accept a "Deliver Bolus" command directly from a user device 310 that follows an approved API set, whereas another medical device manufacturer may opt to, possibly for legacy product reasons, translate the user device data and commands into data and commands that are familiar to that manufacturer's products and services. This configuration may also provide an explicit means for medical device manufacturers to grant or deny certain data and commands from a user device 310, as well as provide extra security and data integrity checks.

In some embodiments, a medical device, such as device 420, may incorporate some or all of the functionality previously described herein with respect to a user device, such as user devices 110, 210 and 310. This may provide enhanced functionality to medical devices to allow them to interface with networks by incorporated functionality traditionally associated with user devices, such as cellular phones. Some of these embodiments may incorporate this functionality in hardware and/or software as a thin client into the medical device to allow it to receive and/or send certified medical applications, updated applications, user/patient data, as well as other applications or information. This may be done by using widely availably infrastructure such as the cellular network and/or Internet.

Service Platform

Figure 5:
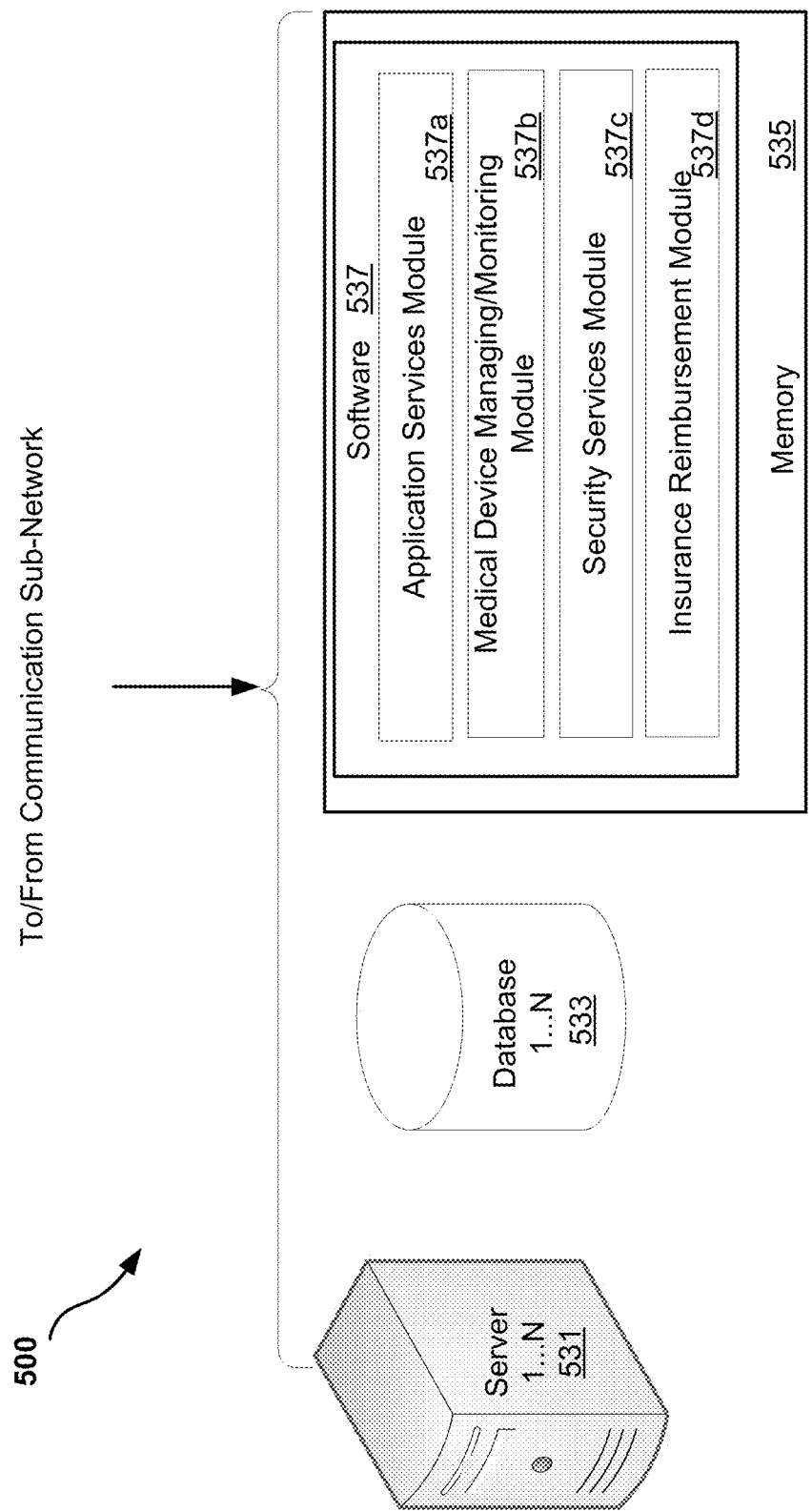
FIG. 5 depicts embodiments of hardware and software architectures that may be implemented in relation to a Service Platform in accordance with aspects of the invention.

FIG. 5 depicts details of an embodiment of a hardware and software architecture for a service platform 530 in accordance with aspects of the present invention. The service platform 530 may correspond to platform 230 of FIG. 2B, and may be be configured to provide a hosted service or any service that offers some or all of the services described herein.

While referring to FIG. 5, simultaneous reference may be made to FIGS. 2-4. Service platform 530 includes one or more servers 531, one or more databases 533 and one or more memory spaces 535 that may comprise one or more physical memory devices. The memory 535 stores a software solution module 537 for carrying out certain aspects of the present invention. The software solution 537 may includes an application services module 537a, a medical device managing/monitoring module 537b, a security services module 537c and an insurance reimbursement module 537d.

The application services module 537a may be configured to operate to receive, maintain and distribute medical applications that are used by the user device 310 (and other devices) to manage/monitor the medical device 420. The databases 533 may be configured to store any number of different medical applications at any one of different phases of development. For example, the databases 533 may store newly-developed, but untested medical applications. After a newly-developed, but untested medical application is uploaded to the databases 533 by a developer, a medical authority (e.g., the FDA and/or a medical application safety authority) can access the medical application to begin a certification process. The certification may include one or more tests of the medical application for compliance with one or more statutory, regulatory and/or industry standard requirements. The databases 533 may also be configured to store testing applications used by a medical authority (e.g., the medical application safety authority) or by the developer to preliminarily test its medical application before submitting it to another medical authority (e.g., the FDA). The databases 533 may also store certified medical applications that may be browsed by a user and eventually downloaded to the user device 210 or 310 and/or medical device 220 or 420. As described herein, a certified medical application is a computer program or other form of executable code or instructions that has been developed for use in a medical device and has undergone testing for compliance with one or more regulatory, statutory or industry regulations, with certification or authorization granted to the medical application as a result of passage of the testing. Once a medical application is certified, version control and restriction on changes to the program become important so as to insure only certified applications can be delivered to a user device or medical device. In addition to storing the medical applications, the databases 533 may store information associated with medical applications that can be accessed by individuals (e.g., the user, a third party).

In accordance with one embodiment, a trusted third party, such as a medical application safety authority (MASA), which is a trusted third party entity separate from the application developer and which has access to or control over a service platform as described herein, may acts as an optional additional layer of security between an application developer and a regulatory agency, such as the United States Food and Drug Administration (FDA). For example, the MASA (distinct from the medical application developer) may receive a medical application from a medical application developer and send the medical application to the FDA for certification. The medical application safety authority may provide preliminarily testing of the medical application before submitted it to the FDA (e.g., for compliance with standards, to ensure integrity of the code, etc) or may submit it directly.

The FDA will then authorize/certify the application (or reject it if non-compliant) based on one or more statutory, regulatory and/or industry standards or requirements. The certified application may then be returned to the MASA. After the FDA certifies a medical application, the MASA may manage the certified medical application during the time it is available to a user. Security associated with this process may be particularly important due to the safety and reliability standards associated with medical devices. Accordingly, this process may be done in a secure, trusted fashion so as to preclude tampering with the certified medical application. In an exemplary embodiment, the MASA prohibits any unauthorized changes by the application developer after certification begins or ends (conversely, tampering or other unauthorized or untested changes frequently happen in the mobile applications world, but cannot be permitted in the medical world due to reliability, safety as well as other requirements).

Figure 13:
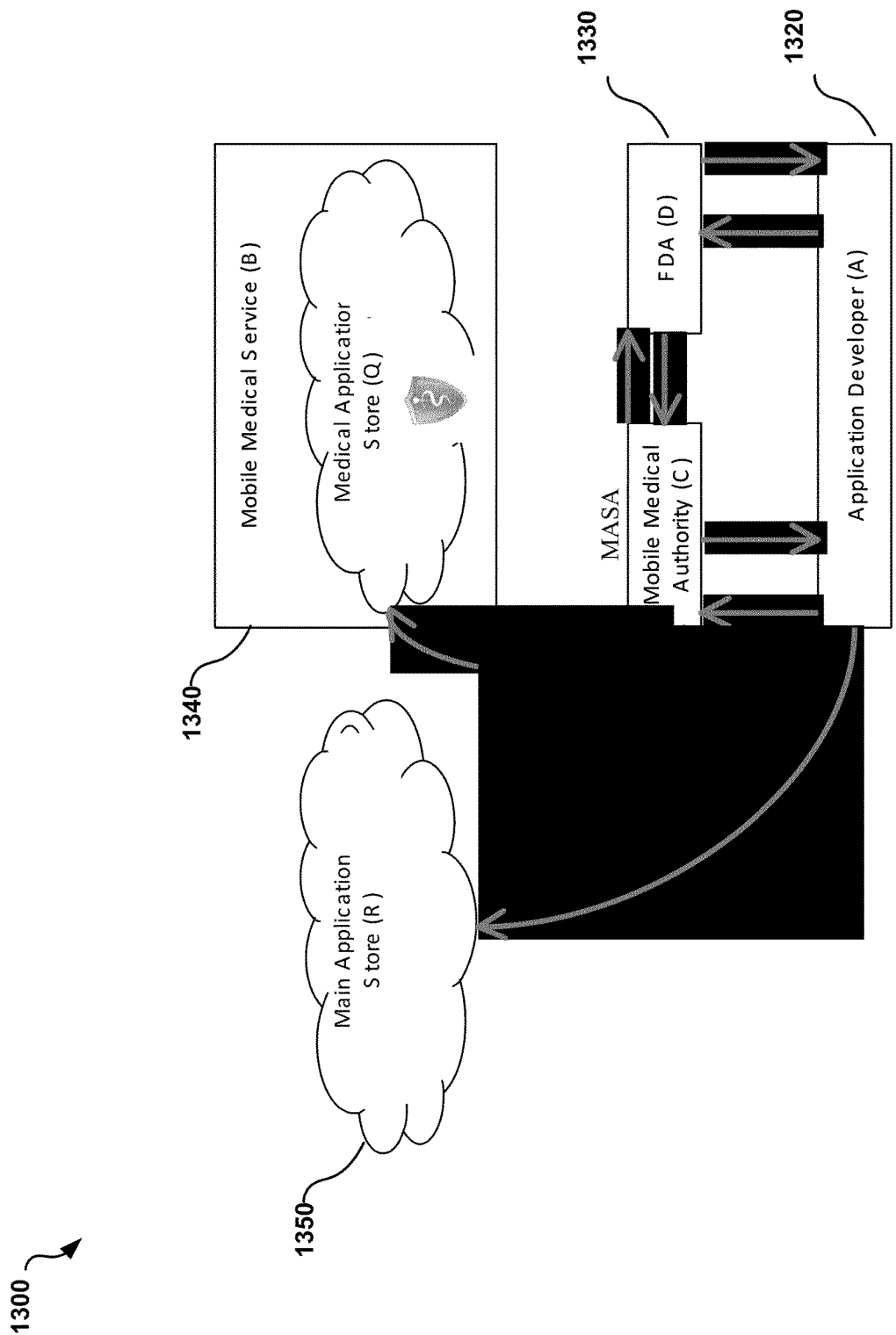
FIG. 13 illustrates an example interaction between an application developer, trusted third party and application stores in accordance with aspects of the invention.

FIG. 13 illustrates an example workflow 1300 among these various entities in accordance with aspects of the present invention. A medical application developer 1320 develops a medical application they wish to provide to users as a certified medical application. This may be done by either providing to a mobile medical authority 1310 (MASA) for interaction with the regulatory authority, in this case the FDA, or may provide it directly to the FDA. If the MASA 1310 is used, the MASA may store the medical application in a secure database as described elsewhere herein and may further perform preliminary testing and/or analysis of the application before submitting it to the regulatory authority. Once submitted, the regulatory authority may either certify the application so as to create a certified medical application, may reject the application, or may require further information, data, etc. The certified application may either be managed directly by the MASA 1310 or may be provided from the regulatory authority 1330 to the developer 1320 and then to the MASA for storage and distribution. In the case of a certified medical application, distribution will typically be tightly controlled and done through a secure medical application store 1340. Provision to the store 1340 is typically only done by a MASA to ensure regulatory compliance and application version control, and likewise, downloading to a user's medical device or user device is typically only done using authentication and user verification to ensure only authorized and appropriate users may download and run the certified medical applications.

The application developer 1320 may also develop non-certified applications, which may be directly distributed to a standard application store 1350. The standard application store may include links or other mechanisms for redirecting users desiring certified medical application to the medical application store 1340

Figure 14:
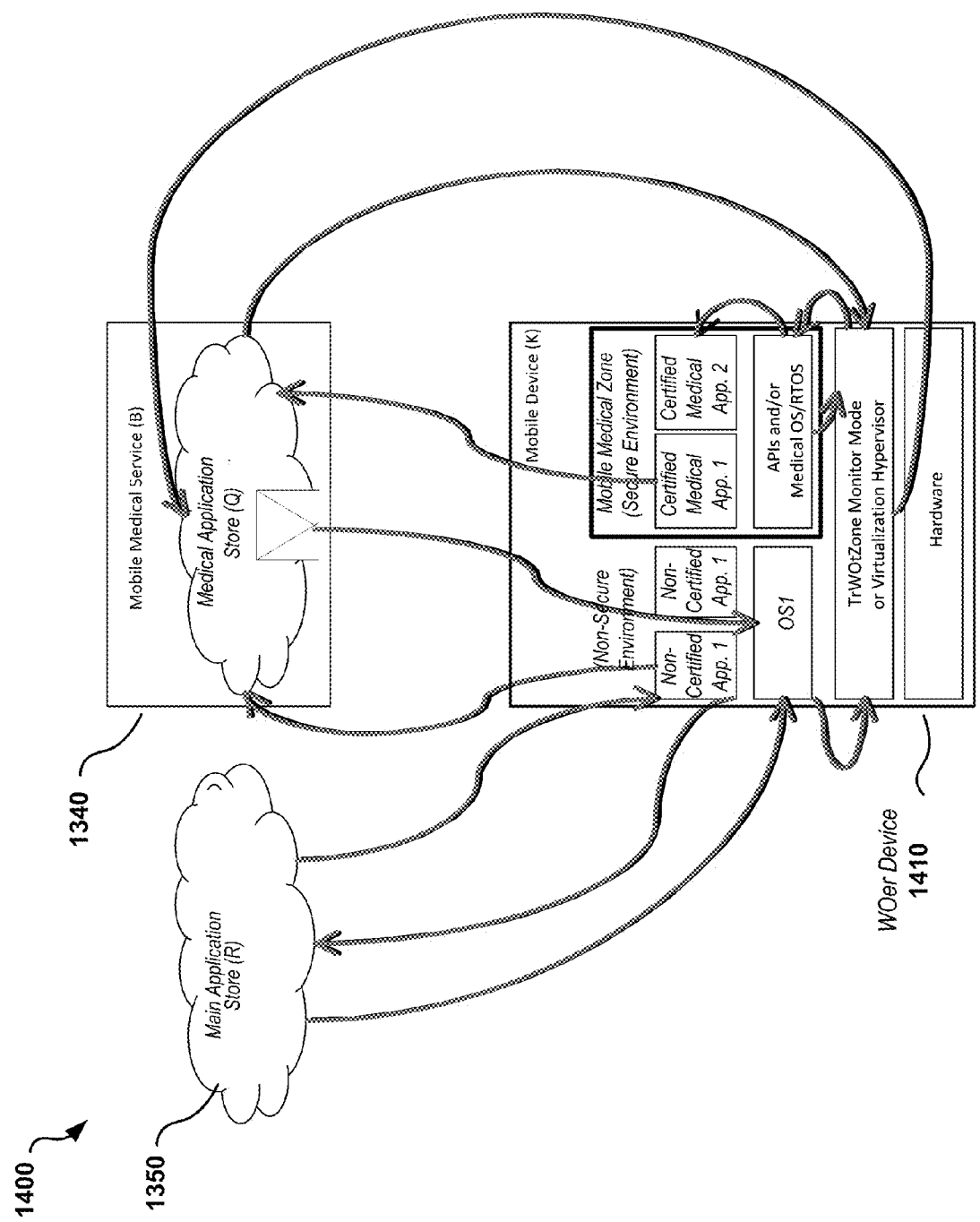
FIG. 14 illustrates an example interaction between a user device and application stores in accordance with aspects of the invention.

FIG. 14 illustrates additional details of interaction between a user device 1410 and application stores 1340 and 1350 as shown in FIG. 13. In particular, user device 1410 includes a secure environment in which only certified medical applications provided from secure medical application store 1340 may be loaded, with corresponding generated data returned only to a secure mobile medical service, which may or may not be associated with the medical application store. User device 1410 includes separate operating systems OSI and Medical OS/RTOS to further separate the secure and non-secure environments. Non-certified applications may be downloaded from store 1350 and may interact with the store and/or other mobile devices or servers (not shown) in the ordinary fashion.

In some embodiments, a medical device may be configured in a fashion similar to user device 1410, with the medical device further including a medical monitoring or control apparatus in addition to the elements shown in FIG. 14. In these implementations, the medical device may communicate directly with the application stores 1340 and 1350 to download applications and send and receive data, without need for an associated user device.

Returning to FIG. 5, medical device managing/monitoring module 537b operates to control the receipt/sending of data from/to various devices in accordance with managing or monitoring the medical device 420. For example, when an individual (e.g., the user, a third party, etc) initiates a request to view and/or manipulate data associated with the medical device 420, the medical device managing/monitoring module 537b coordinates the accessing, transferring, buffering, viewing and manipulation of the requested data. The medical device managing/monitoring module 537b also coordinates the receipt and transferring of an individual's command to the medical device 420.

Security services module 537c operates to control various security-related aspects of the invention. For example, the security services module 537c may control the selection and distribution of one or more security applications to the user device 310 and medical device 420. The one or more of the security applications, which are stored in the databases 533, provide for secure communication among a particular medical device 420, a particular user device 310 and the service platform 530. The security applications may be selected by operations of the security services modules 537c at random or at preconfigured times. Alternatively, the module 537c may autonomously create a custom security application. Once selected, the security application is pushed to the user device 310 and/or the medical device 420 via the communication sub-network 240. Once downloaded, the security application runs on each device/platform to ensure secure (e.g., encoded, encrypted, etc) communications.

Security services module 537c also ensures the integrity of the secure environment 311 and medical applications on the user device 310, as well as the secure environment and the medical applications on the medical device 420 (if applicable). The security services module 537c carries out these functions by utilizing common and/or custom techniques involving check sums, sample code reads and running a short test program, digital rights management (DRM) among others.

Insurance reimbursement module 537d is configured to monitor medical device and medical application usage by plan type/ID, plan amount, subscriber, etc. The module 537d may also be configured to provide an interface that insurance companies can use to electronically access the usage data. The user device 310, secure environment 311, medical applications, medical device 420 (and secure environment) may be assigned insurance billing codes that can be used to track usage for billing and reimbursement purposes.

Network Configurations

Figure 6:
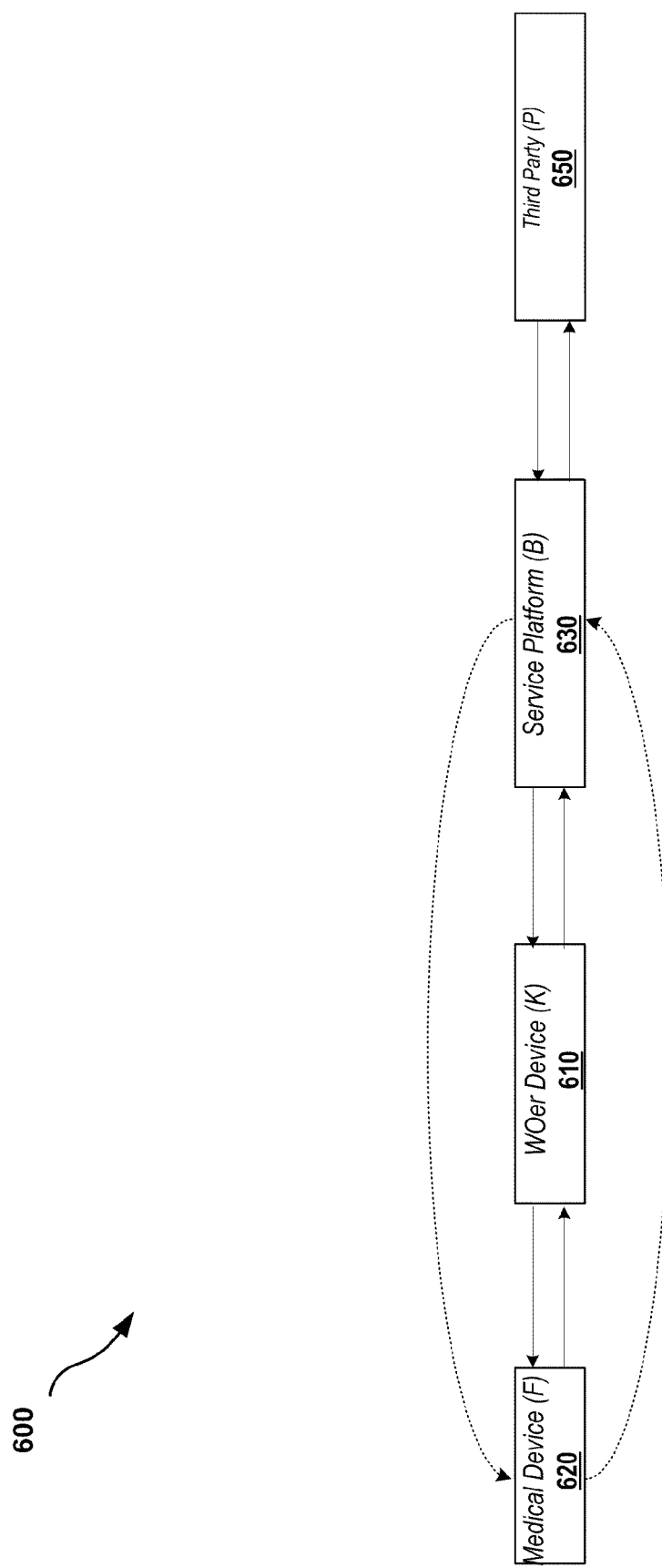
FIG. 6 illustrates an embodiment of a communication configuration 600 in accordance with aspects of the invention.

FIG. 6 illustrates an embodiment of a communication configuration 600 in accordance with aspects of the present invention. The communication configuration 600 includes a user device 610, a medical device 620, a service platform 630 and one or more third parties 650. These may correspond to the analogous devices shown in FIGS. 2-4. For the sake of simplicity and clarity, middleware and other communication sub-network components are not included in the communication configuration 600, however, they will be present in typical implementations.

In accordance with FIG. 6, uploading and synchronization of information (e.g., collected at the medical device 620) or medical applications (e.g., running on the user device 610 or medical device 620) can be carried-out automatically and/or via user or third-party request. As shown in FIG. 6, any of the four devices/platforms 610, 620, 630 and 650 can request information from or transfer information to any of the other device/platforms. The transmission of the information or medical applications may be accomplished using encryption or other techniques (e.g., TCP/IP, SSL, IPSec, VPN, HTTPS, among others) to ensure privacy and integrity in relation to the contents of the transmission.

When a transfer of transmission of the information or medical applications uses a gateway, such as when the medical device 620 uses the user device 610 to transfer data to the service platform 630, or when a third party 650 requests information from a user device 610 via the service platform 630, the transmitted data may pass through a secure zone such as the secure environment 311 on the user device 610, or a similar secure environment on the service platform 630. Data passing through a gateway configuration may or may not be buffered to protect against connectivity loss on any of the post-gateway links with or without the help of standards such as but not limited to IPSec, SSL, HTTPS, VPN, embedded security such as in Bluetooth for example, encryption (such as but not limited to 128 bit or higher, RSA, etc.). The gateways may or may not have the ability and/or permission to decrypt the data.

One of skill in the art will appreciate the various communication configurations needed to transmit data, information and applications among the devices/platforms/sub-networks of the present invention.

Figure 7:
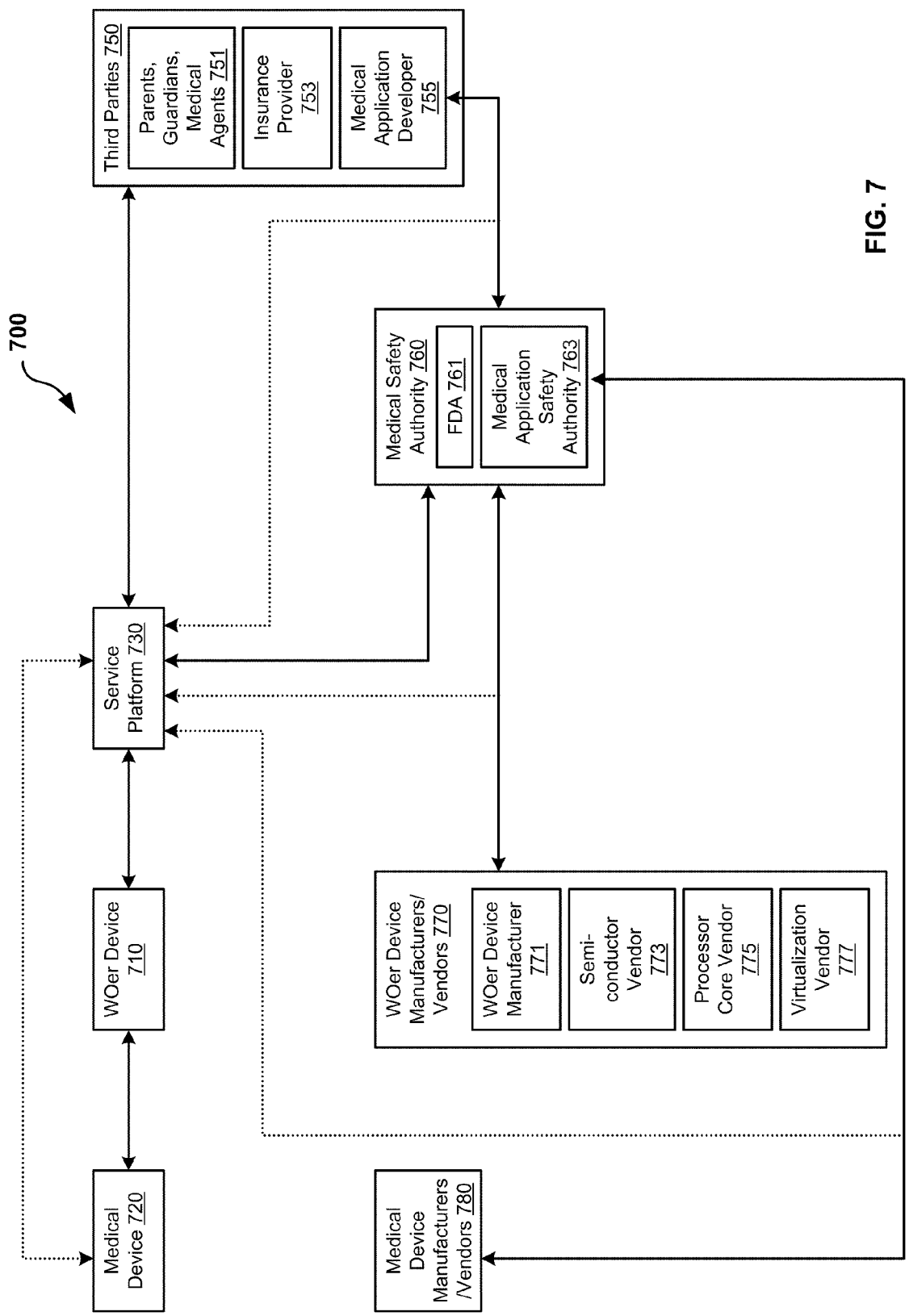
FIG. 7 illustrates an embodiment of a communication configuration 700 in accordance with aspects of the invention.

FIG. 7 illustrates a communication configuration 700 in accordance with at least one embodiment of the present invention. The communication configuration 700 includes a user device 710, a medical device 720, a service platform 730, a communication sub-network 740, third parties 750, a medical safety authority 760, user device manufacturer/vendors 770 and medical device manufacturer/vendors 780. The third parties 750 include one or more parents/guardians/medical agents 751, and insurance provider 753 and a medical application developer 755. The medical safety authority 760 includes the FDA 761 and the medical application safety authority 763. The user device manufacturer/vendors 770 include a user device manufacturer 771, a semiconductor vendor 773, a processor core vendor 775 and a virtualization vendor 777.

By way of example, the following process flow relates to certain aspects of the present invention. The process flow describes certain actions taken by devices/platforms/sub-networks depicted in FIG. 7.

(1) The medical application developer 755 (e.g., a medical application developer, a medical device manufacturer 780, etc) requests a Software Development Kit (SDK) from the service platform 730 (or alternatively from the medical safety authority 760 (not shown)). The request may include information pertinent to the authorized distribution of the SDK (e.g., company name, address, point of contact, email address, requested user name and password, payment information, etc).

(2) The service platform 730 (or the medical safety authority 760) delivers the or access to the SDK via the communication sub-network 740 (e.g., via email, CD, a link to a download site with credentials, etc).

(3) The medical application developer 755 develops a medical application, tests the medical application and submits the medical application to the medical safety authority 760 for approval. The submission to the medical safety authority 760 may be accomplished via a service and equipment hosted by the service platform 730 or via a service and equipment hosted by the medical safety authority 760.

(4) The medical safety authority 760 grants or denies approval of the submitted medical application based on predetermined criteria (e.g., industry standards, government regulations (processes for granting approval by the FDA 761), fail-safe and security requirements, etc). One of skill in the art will appreciate that one or more medical safety authorities 760 (e.g., the FDA 761, the medical application safety authority 763) may be involved in the approval processes for a medical application. Such approval processes may include preliminary screening of medical applications prior to the start of certification testing procedures. The approval processes may also provide for participation by the medical application developer 755.

(5) The medical safety authority 763 uploads approved medical application to a service hosted by the service platform 730, the service being accessible by users and/or third parties for downloading to their computing devices (e.g., the user device 710).

(6) Once an approved medical application is uploaded, the service platform 730 sends an acknowledgement.

(7) The medical safety authority 760 then acknowledges the successful uploading of the medical application to the medical application developer 755.

By way of another example, the following process flow relates to certain aspects of the present invention. The process flow describes certain actions taken by devices/platforms/sub-networks depicted in FIG. 7.

(1) The medical device manufacturer 780 requests the Software Development Kit (SDK) from the medical safety authority 760. The request may include information pertinent to the authorized distribution of the SDK (e.g., company name, address, point of contact, email address, requested user name and password, payment information, etc).

(2) The service platform 730 (or the medical safety authority 760) delivers or provides access to the SDK via the communication sub-network 740 (e.g., via email, CD, a link to a download site with credentials, etc).

(3) The medical device manufacturer 780 develops a medical application, tests the medical application and submits the medical application to the medical safety authority 760 for approval. The submission to the medical safety authority 760 may be accomplished via a service and equipment hosted by the service platform 730 or via a service and equipment hosted by the medical safety authority 760.

(4) The medical safety authority 760 grants or denies approval of the submitted medical application based on predetermined criteria (e.g., industry standards, government regulations (processes for granting approval by the FDA 761), fail-safe and security requirements, etc). One of skill in the art will appreciate that one or more medical safety authorities 760 (e.g., the FDA 761, the medical application safety authority 763) may be involved in the approval processes for a medical application. Such approval processes may include preliminary screening of medical applications prior to the start of certification testing procedures. The approval processes may also provide for participation by the medical device manufacturer 780.

(5) The medical safety authority 763 uploads approved medical application to a service hosted by the service platform 730, the service being accessible by users and/or third parties for downloading to their computing devices (e.g., the user device 710).

(6) Once an approved medical application is uploaded, the service platform 730 sends an acknowledgement.

(7) The medical safety authority 760 then acknowledges the successful uploading of the medical application to the medical device manufacturer 780.

Similar process flows may be applied with respect to other devices/platforms/configuration entities. For example, a similar process for developing, gaining approval and uploading a medical application is applied to the user device manufacturer/vendor 770. Each of the user device manufacturer 771, semiconductor vendor 773, processor core vendor 775 and virtualization vendor 777 may independently or collaboratively proceed through a similar process flow to that of the medical application developer 755 and the medical device manufacturer 780 in relation to development and approval of medical applications, secure environments and secure transmission of data to/from the user device 710. The medical safety authority 760 may also be configured to test and approve security applications and processes, as well as.

Figure 8:
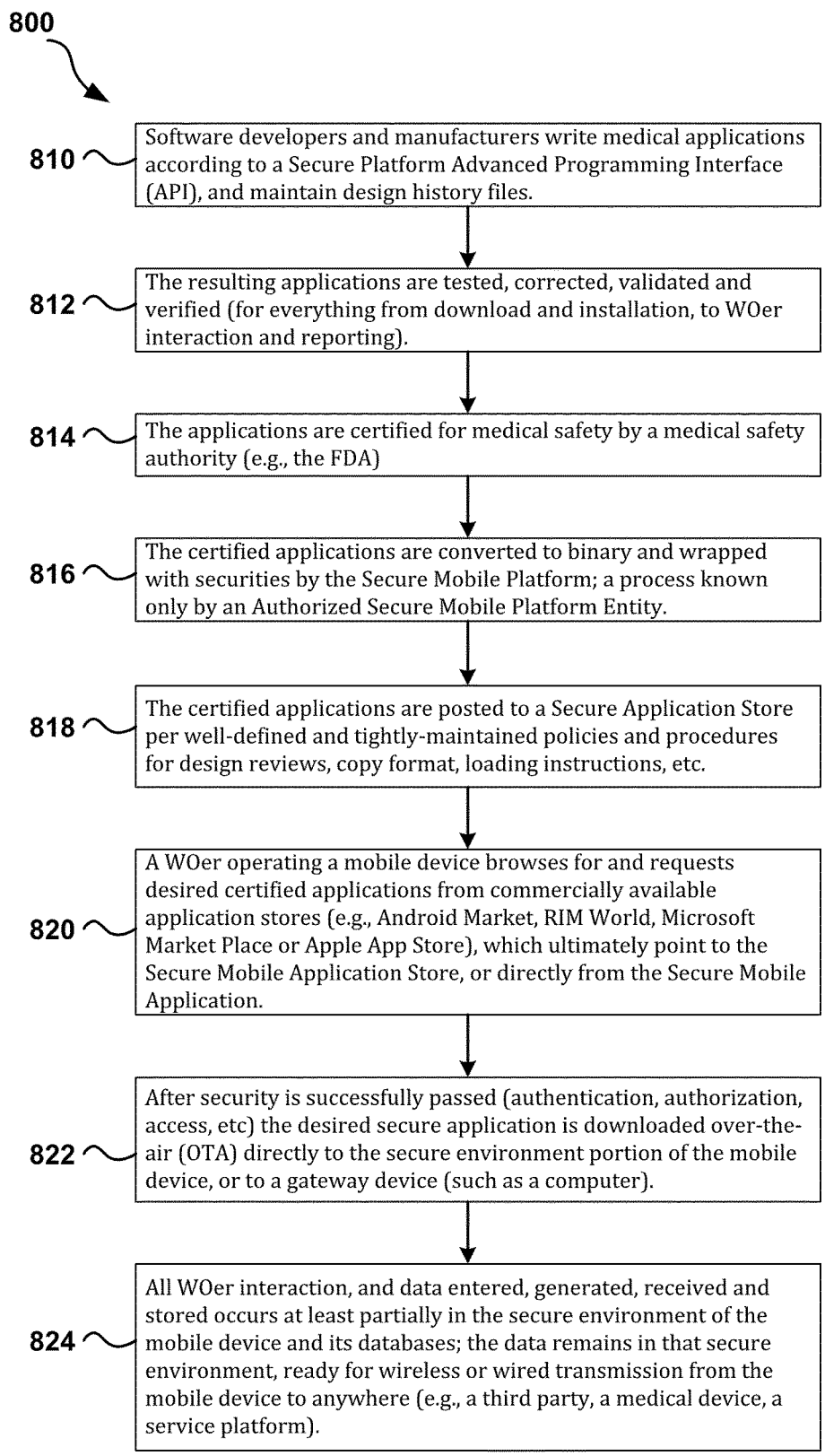
FIG. 8 shows an exemplary process flow that may be carried-out in a similar configuration to that of the communication of FIG. 7.

By way of example, FIG. 8 shows a process flow 800 in accordance with one embodiment of the invention. The process flow 800 may be carried-out in a similar configuration to that of the communication configuration 700 of FIG. 7. Process flow 800 may begin at stage 810, where a medical application developer writes a medical application for ultimate provision to a user device, such as user device 210. The application may be written to conform to a Secure Platform Advanced Programming Interface (API) and maintain design history files. The application may then be provided to a trusted third party, such as a MASA described previously herein, where it may optionally be tested, corrected validated and/or verified. The medical application may then be provided to an appropriate regulatory authority, such as the FDA, for certification. At stage 814, the application may be certified based on particular statutory, regulatory and/or industry requirements. The application may then be packaged for provisioning at stage 816. In particular, in an exemplary embodiment, the certified applications are converted to binary and wrapped with securities. This may be done by the Secure Mobile Platform fur further provisioning. At stage 818, the certified applications may be provided to a user directly or may be provided to and posted on a Secure Application Store (SAS). This store may be analogous to currently available online application sites, such as those provided by Apple, Inc. or others. However, because of the security and reliability requirements imposed on medical applications, the SAS should be configured to operate in accordance with well-defined and tightly maintained policies and procedures for details such as design reviews, copy format, loading instructions, and the like.

Users will generally have access through their user devices or other devices (such as personal computers, etc.) to the SAS, where they may be able to browse, at stage 820 for certified applications. Commercial application providers, such as those provided for Android, RIM, Microsoft, Apple or other application providers may include a link or other mechanism for redirecting users to the SAS. At stage 822, a user will be subject to SAS access security procedures to authenticate, authorize and access associated certified medical applications. The desired and approved or authorized application (which may be based on medical provider criteria, insurance company criteria, or other security or verification criteria) may then be directly downloaded, over the air, to the user's device, such as device 210 of FIG. 2A. The certified medical application may then be provisioned in the secure environment of the user's device, where it is then executed at stage 824, typically at least partially within the secure environment.

Figure 9:
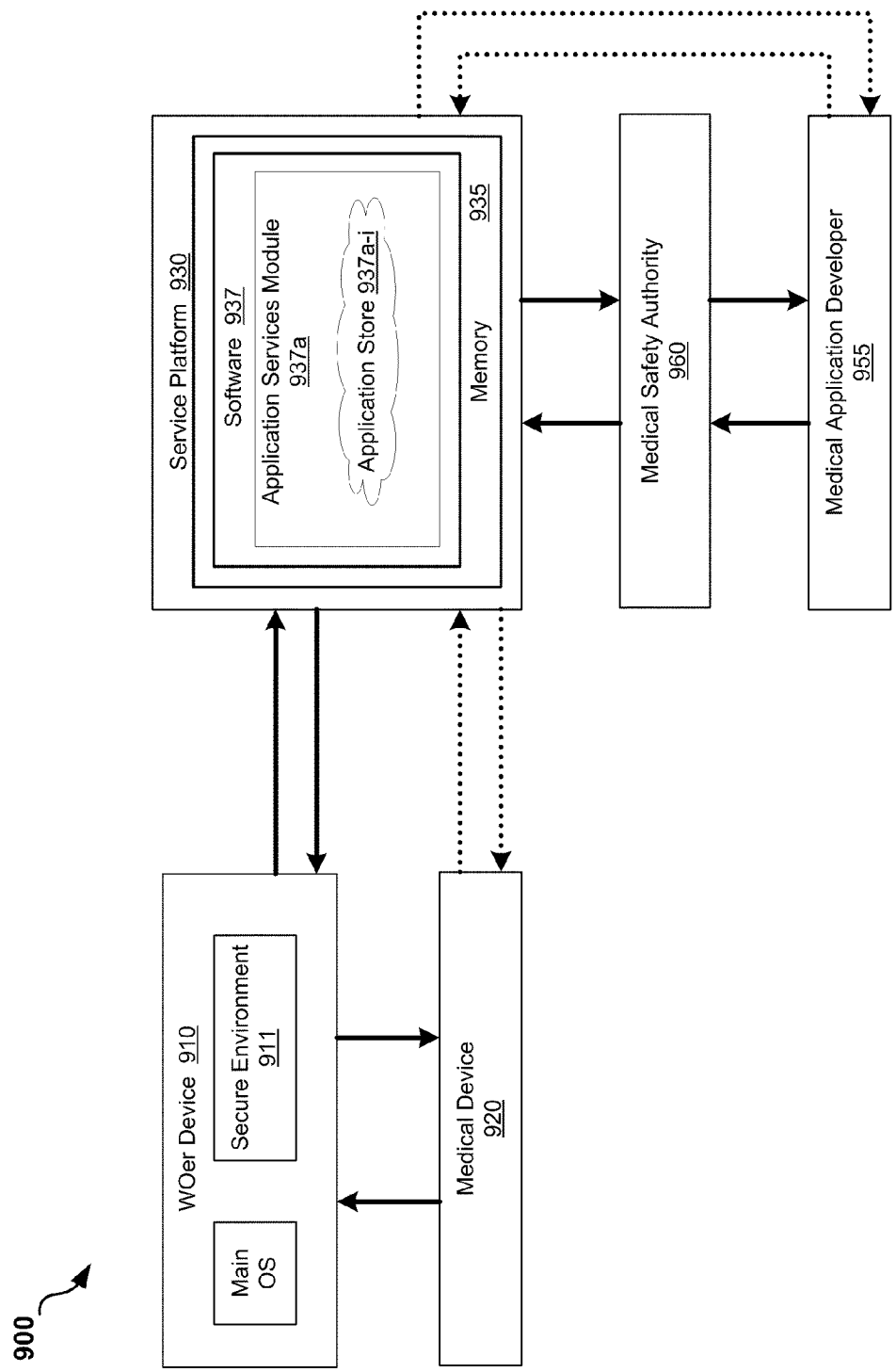
FIG. 9 illustrates an embodiment of a process 900 for developing a medical application for operation on a user device and/or medical device in accordance with aspects of the invention.

FIG. 9 illustrates an embodiment of a network configuration 900 for providing a medical application that can be browsed for by user device and/or medical device in accordance with aspects of the present invention. The network configuration 900 includes a user device 910, a medical device 920, a service platform 930, an application developer 955 and a medical safety authority 960 (e.g., the FDA). The service platform 930 includes a memory 935, on which a software solution 937 runs. The software solution 937 runs an application services module 937a. The application services module 937a provides a medical application store (e.g., similar to Apple's iTunes, Blackberry Rim World, Microsoft Marketplace, etc). Medical applications may be browsed and selected by a user operating the user device 910. For example, the user may browse and download via a Main OS (e.g., Android, Apple, BREW, Java, Linux, RIM, Symbian, Windows Mobile, etc), or direct from the secure environment 311. In accordance with this embodiment, downloading may involve encryption techniques and/or Digital Rights Management (DRM) known in the art. Decryption could then take place within or outside the secure environment 911. Alternatively, the user device 910 and/or medical device 920 may automatically select or receive a medical application without user intervention through a script for example.

In one embodiment, applications are downloaded and run from the main OS, but the critical, secure related features (e.g., changing settings in the medical device 920) are managed in the secure environment 911. Care must be taken to ensure that the applications are authentic, were downloaded completely and that they maintained their integrity. One method for accomplishing is to push the downloaded application to the secure environment 911, copy it, and send it from the secure environment 911 and/or from the main OS to a secure environment on the service platform 930, where copies of valid medical applications are stored. These copies can be used to authenticate the downloaded files. This process may take place at any point during the operational life of the medication application to periodically ensure the authenticity and integrity of the application. Another process to ensure the integrity of a medical application is to run a simulation between the user device 910 and the service platform 930, where the service platform 930 simulates the medical device 910. If the authentication process fails, or another problem is detected, the service platform 930 may prohibit the use of that medical application. This process can also be periodically performed to maintain and assure the quality of applications as they are used over time, even after they are initially authenticated.

Figure 10:
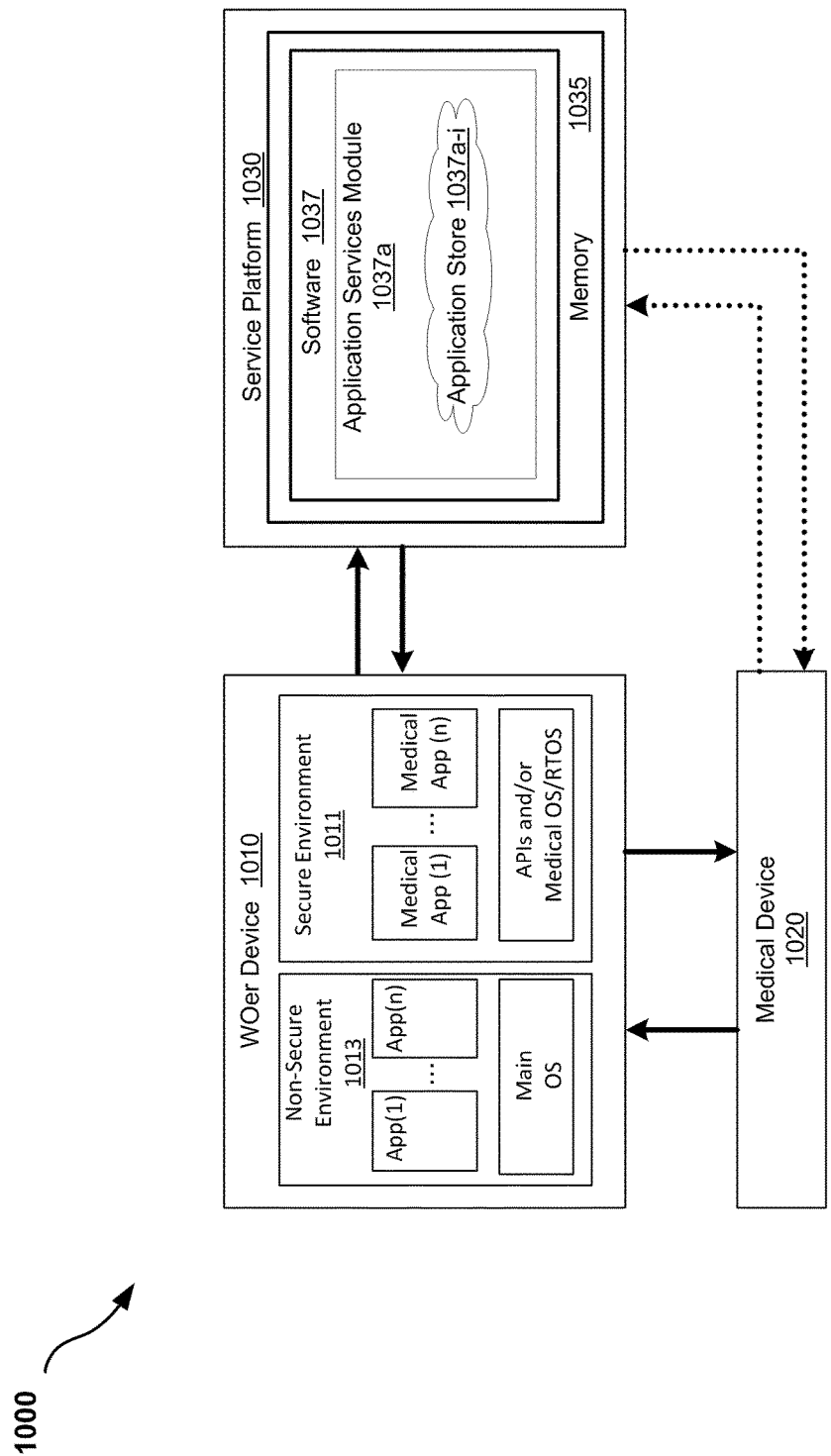
FIG. 10 describes an embodiment of a process 1000 for downloading a medical application to a user device in accordance with aspects of the invention.

FIG. 10 illustrates an embodiment of a network configuration 1000 for downloading a medical application to a user device in accordance with aspects of the present invention. The network configuration 1000 includes a user device 1010 and a service platform 1030. The service platform 1030 includes a memory 1035, on which a software solution 1037 runs. The software solution 1037 runs an application services module 1037a. The application services module 1037a provides a medical application store 937a-i (e.g., Apple Store, Blackberry Rim World, Microsoft Marketplace, etc). Medical applications may be browsed and selected by a user operating the user device 1010.

In accordance with one embodiment, an application on the user device 1010 runs in conjunction with a main operating system (OS) to enable a user to browse medical applications that are accessible via the medical application store 1037a-i. An alternative embodiment allows the user device 1010 to browse the medical applications without user intervention. After a medical application is selected, an encrypted version of that medical application is downloaded to the main OS. The first instruction of the recently downloaded application is to move it from the main OS to the secure environment 1011. After the medical application is moved into the secure environment 1011, the secure environment 1011 sends an exact copy of the medical application to the service platform 1030, and waits for the service platform 1030 to authenticate that exact copy via a digital certificate. The authentication ensures that the user device 1010 downloaded a complete and uncorrupted version of the medical application. After the service platform 1030 authenticates the copy of the medical application, the secure environment 1011 proceeds to decrypt and install the medical application in the secure environment 1011. Alternatively, the secure environment 1011 may securely pass the medical application to the medical device 1020, at which point a similar authentication process occurs between the medical device 1020 and the service platform 1030 (via direct connection or via the user device 1010 as a gateway). Alternative embodiments may not require the authenticity and integrity check with the service platform 730.

In accordance with one embodiment, applications are downloaded and run from the main OS, but the critical, secure related features (e.g., changing settings in the medical device 1020) are managed in the secure environment 1011. Care must be taken to ensure that the applications are authentic, were downloaded completely and that they maintained their integrity. One method for accomplishing this would be to push the downloaded application to the secure environment 1011, copy it, and send it from the secure environment 1011 and/or from the main OS to a secure environment on the service platform 1030, where copies of valid medical applications are stored. These copies can be used to authenticate the downloaded files. This process may take place at any point during the operational life of the medication application to periodically ensure the authenticity and integrity of the application. Another process to ensure the integrity of a medical application is to run a simulation between the user device 1010 and the service platform 1030, where the service platform 1030 simulates the medical device 1010. If the authentication process fails, or another problem is detected, the service platform 1030 will prohibit the use of that medical application. This process can also be periodically performed to maintain and assure the quality of applications as they are used over time, even after they are initially authenticated.

Figure 11:
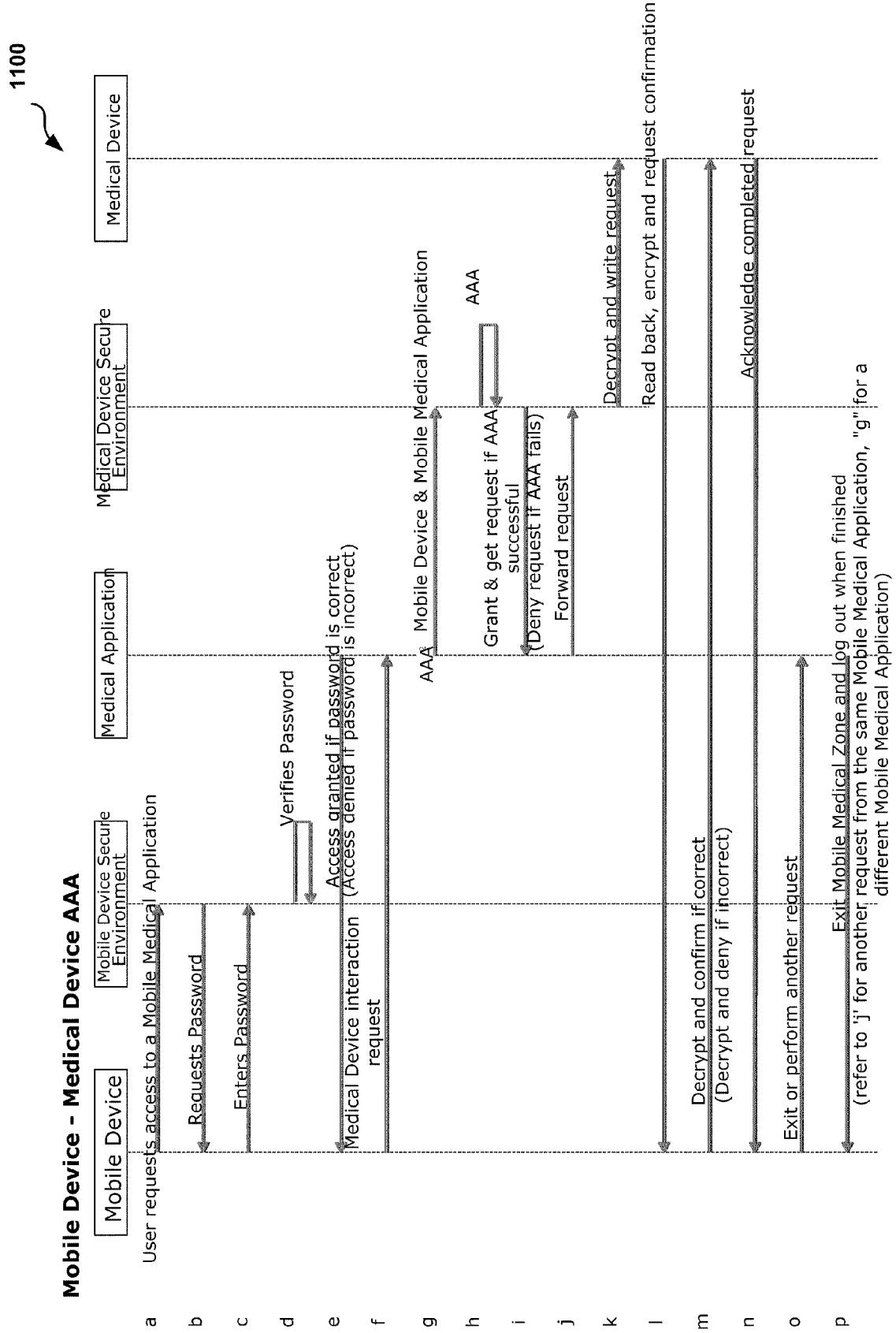
FIG. 11 shows an embodiment of a process flow 1100 in relation to communication between a user device and medical device in accordance with aspects of the invention.

FIG. 11 shows an embodiment of a process flow 1100 in accordance with aspects of the invention. The process flow 1100 illustrates communication between a user device (e.g., a mobile device) and a medical device.

Figure 12:
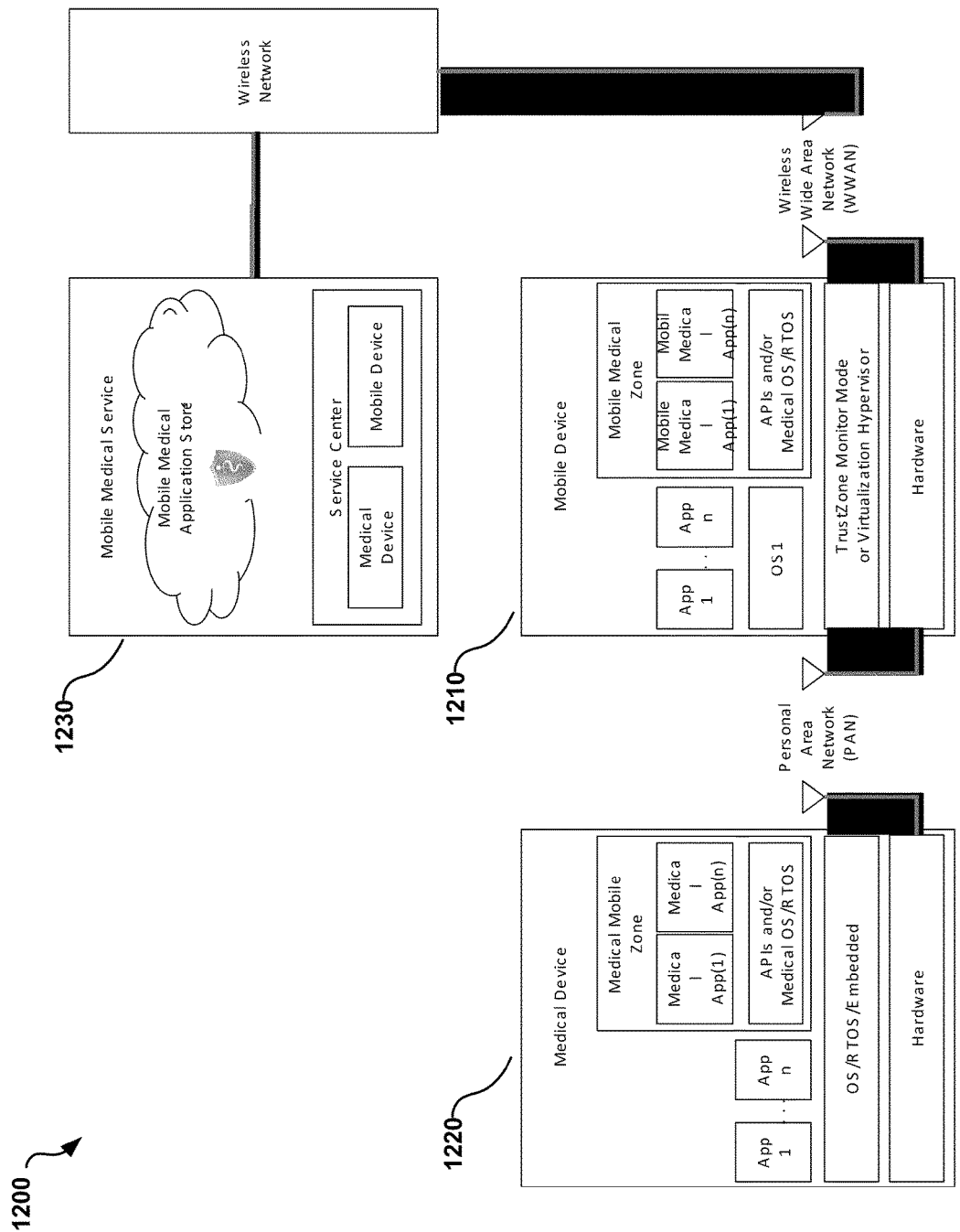
FIG. 12 illustrates an embodiment of a system including a medical device, user device and service platform in accordance with aspects of the invention.

FIG. 12 illustrates details of an embodiment 1200 of a medical device 1210 in communication with a user device 1220 via a PAN, with the user device 1220 further coupled, via a wide area network (WAN) to an application store 1230, which may be part of or incorporated in a service platform, such as service platform 230 of FIG. 2B.

Figure 15:
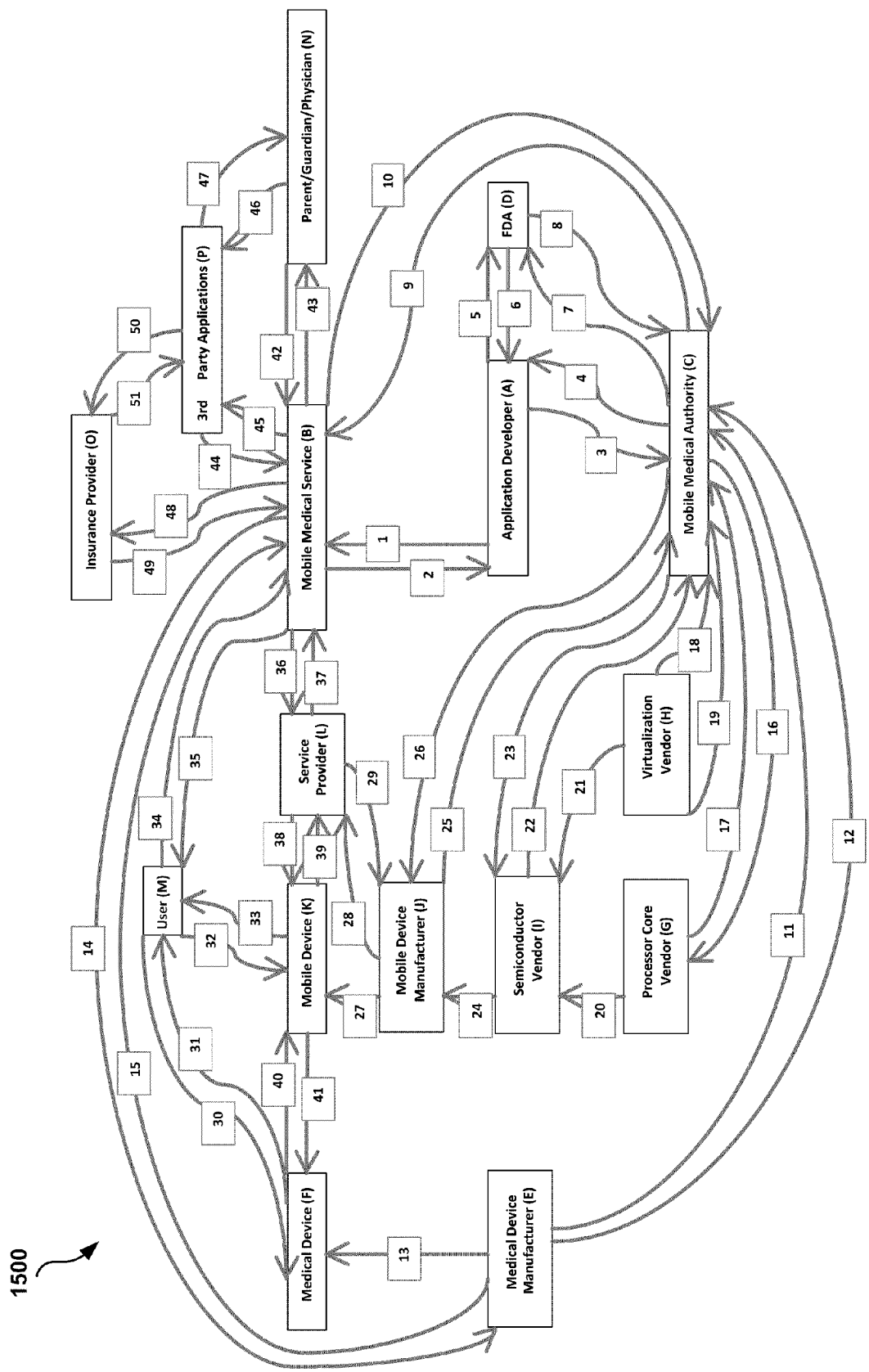
FIG. 15 illustrates interaction between various entities associated with provision of certified medical application.

FIG. 15 illustrates details of an embodiment of a system and associated interaction between various elements as were described previously herein.

Additional features of various embodiments may include one or more of the following:

A medical device, including functionality described herein in conjunction with a user device, with the medical device provided with preloaded, non-certified consumer applications (e.g. phone, calendar, email, internet, camera, navigation, social networking, etc.). In addition, the medical device may include one or more preloaded certified medical applications.

A medical device, including functionality described herein in conjunction with a user device, that is configured with the ability to download medical and/or consumer applications wirelessly or via a cable, via directly through a user interface on the medical device itself, or via a secondary device such as a mobile computer or other user device.

A medical device, including functionality described herein in conjunction with a user device, that is configured that is configured with two or more separate operating environments, where one such environment is a secure environment for hosting certified medical applications (e.g. reading data from a continuous blood glucose sensor, controlling an insulin pump, medication compliance reminders, food libraries, heart monitoring via sensors, internal defibrillators, pacemakers and the like), and the other unsecured environment(s) hosts consumer applications, though within one common physical device. In accordance with the details described previously herein, the medical device would be configured so that only the secure medical environment would be considered the medical device by definition and only that secure environment would be held accountable to medical standards and regulations (e.g. FDA, HIPAA, etc.), whereas non-medical environments would not be under medical standards and regulations and could consequently readily receive and execute standard, non-certified applications.

As described previously, in some embodiments, a medical device or user device may be configured to partially shut down depending on operating circumstances. For example, the device may include the the ability to turn off/disable the some or all consumer applications (to save power, not be disturbed while sleeping, enter flight mode per FAA guidelines, etc.) so as to insure reliability, guarantee performance, save power to extend operational life, securely shut-down and/or provide other safety or reliability functionality. Likewise, the device may be able to turn off part of the provided communications capability, such as by turning off WAN or cellular connectivity while retaining PAN connectivity.

In some embodiments, a medical device or user device may be configured with the ability to turn off/disable one or more, or all environments other than the secure environment that hosts the certified medical applications. In addition, the devices may be configured with the ability to turn off/disable all wireless radios, or all wireless radios other than those used to communicate to medical devices (again to save power, not be disturbed while sleeping, enter flight mode per FAA guidelines, etc.)

In some embodiments, a medical device or user device may be configured with the ability to set priority between medical applications and consumer applications, regardless of other system priority configurations or settings. In addition, the devices may be configured with the ability to set priority between individual features within applications (e.g. a low blood glucose alert may supersede everything, a medication compliance reminder may share priority with consumer calendar application reminder, delivering a bolus of insulin may or may not reject an incoming phone call, etc.).

In some embodiments, a medical device or user device may be configured with the ability to alter (upgrade, modify, reinstall, replace, etc.) anything not within the medical environment (e.g. non-medical environment, applications within such an environment, drivers within or for such an environment, hardware for such an environment, etc.) without modifying the medical environment/medical device, and hence not requiring additional testing, verification, validation, etc. for medical device clearance.

In some embodiments, a medical device or user device may be configured with the ability for creation, commercialization and de-commercialization of mobile medical applications. In this case, the medical application developer requests and registers for a software development kit (SDK) from a medical application clearing house (MACS), with an SDK provided after successful registration, etc. Using the SDK, the application developer develops the application, submits it to the MACS, the MACS may or may not provide a prescreening of the application to test functionality, etc. The MACS then stores a copy of the application and submits a copy of the application to any necessary regulatory bodies (e.g. FDA) on behalf of the application developer. Only upon regulatory approval/certification can the MACS make the application available for download, and only the MACS (not the application developer) has access to upload applications for download to medical devices (this ensures that the application has not been modified since submitted to regulatory bodies). The MACS also has the ability and authority to immediately remove applications from download at the request of the application developer, a regulatory body concern (e.g. a recall), a business issue with the application developer, etc. An upgrade or enhancement would then typically follow the same commercialization process.

In some embodiments a medical device or user device may be configured to store health records in the device. This may include, for example, any data captured, created, modified, etc. due to any component of the medical environment may be stored in a local health record/database. This database may be preconfigured with privacy, security and encryption techniques, and possibly depersonalization techniques per the decision of the developer and or regulatory guidelines (e.g. HIPAA). For example, when a user changes their Basal rate for their insulin pump, the change may be date and time stamped, and sent to the local health record. On the way to the local health record, the user's name and other personal information may or may not be removed for privacy, and the data may use an encryption technique (e.g. RSA) to encrypt the data. Additional rules may also be applied such as a limitation on how long the data may be stored in the device, when the data is removed (e.g. once uploaded to a remote health record (e.g. a PHR such as Google Health, Microsoft Vault, etc., or an EHR such as those provided by Epic, Allscripts, etc.).

In some embodiments a medical device or user device may be configured for clearing a user's health record. Due to the sensitivity, regulations and importance of the data, the health record data may be cleared remotely at the request of the user. It may also be cleared if a predetermined number of faulty attempts have been made to log into the device. Additionally, instead of simply clearing the health record data, it may optionally be automatically uploaded to a remote health record site prior to being cleared from the device.

In some embodiments, a medical device or user device may be configured as a slave device. For example, the actual medical device, perhaps a small body worn device, for example, hosts and runs the application(s). The user device, perhaps a mobile phone or eReader or personal computer, for example, uses the aforementioned medical environment to securely project a user interface for the user to interact with the medical device.

In some embodiments, a medical device or user device may be configured as a Medical Environment Indicator. As a precautionary measure, an indicator, such as an LED, display indicator, buzzer, flashing light, or other form of audible, tactile and/or visual indication will be actuated to notify the user when they are running an application in the medical environment, and when they are not. This may be used to help protect from ghost applications that pretend to be medical applications and hence confuse the user. Additional details of management of medical devices using a cell phone are described in U.S. patent application Ser. No. 12/239,906, entitled "Cell Phone Remote Disease Management," filed Sep. 29, 2008, which is incorporated herein by reference in its entirety.

The term "exemplary" is used herein to mean "serving as an example, instance, or illustration." Any embodiment described herein as "exemplary" is not necessarily to be construed as preferred or advantageous over other embodiments.

It is noted that in various embodiments the present invention relates to one or more methods or processes such as are described and/or illustrated herein. These processes are typically implemented in one or more modules as are described herein, and such modules may include computer software stored on a computer readable medium and/or in a computer memory or other instruction storage device, including instructions configured to be executed by one or more microprocessors or other digital instructions execution mechanisms to perform the described process steps or stages.

It is further noted that, while the processes described and illustrated herein may include particular steps or stages, it is apparent that other processes including fewer, more, or different stages than those described and shown are also within the spirit and scope of the present invention. Accordingly, as noted previously, the processes and associated modules shown herein are provided for purposes of illustration, not limitation.

Some embodiments of the present invention may include computer software and/or computer hardware/software combinations configured to implement one or more processes or functions associated with the present invention such as those described herein. These embodiments may be in the form of modules implementing functionality in software and/or hardware software combinations. Embodiments may also take the form of a computer storage product with a computer-readable medium having computer code thereon for performing various computer-implemented operations, such as operations related to functionality as described herein. The media and computer code may be those specially designed and constructed for the purposes of the present invention, or they may be of the kind well known and available to those having skill in the computer software arts, or they may be a combination of both.

Examples of computer-readable media within the spirit and scope of the present invention include, but are not limited to: magnetic media such as hard disks; optical media such as CD-ROMs, DVDs and holographic devices; magneto-optical media; and hardware devices that are specially configured to store and execute program code, such as programmable microcontrollers, application-specific integrated circuits ("ASICs"), programmable logic devices ("PLDs") and ROM and RAM memory devices. Examples of computer code may include machine code, such as produced by a compiler or other machine code generation mechanisms, scripting programs, PostScript programs, and/or other code or files containing higher-level code that are executed by a computer using an interpreter or other code execution mechanism.

Computer code may be comprised of one or more modules executing a particular process or processes to provide useful results, and the modules may communicate with one another via means known or developed in the art. For example, some embodiments of the invention may be implemented using assembly language, Java, C, C#, C++, scripting languages, and/or other programming languages and software development tools as are known or developed in the art. Other embodiments of the invention may be implemented in hardwired circuitry in place of, or in combination with, machine-executable software instructions.

It is understood that the specific order or hierarchy of steps in the processes disclosed are examples of exemplary approaches. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein. It is intended that the following claims and their equivalents define the scope of the invention.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c.

It is intended that the following claims and their equivalents define the scope of the invention.

I claim:

1. A computer-implemented method of interacting with a medical device in wireless communication with a user device, comprising:
   receiving, at the user device, a certified medical application wherein the user device is physically separated from the medical device and includes:
   a secure environment processor included within a secure environment of the user device wherein the secure environment is provided with guaranteed processor and memory resources in the event of at least one of a denial of service attack and an attempt to overload processing or memory usage in the secure environment,
   a nonsecure environment processor wherein the secure environment processor is physically isolated from the nonsecure environment processor,
   a secure environment memory coupled to the secure processor and accessible only to the secure environment processor, the secure environment memory being included within the secure environment and including a security monitor executed by the secure environment processor wherein the security monitor is configured to:
      identify secure traffic on the user device wherein the secure traffic is associated with a function of the certified medical application requiring security,
      identify a security requirement associated with the function,
      manage execution of the certified medical application within the secure environment in accordance with the security requirement,
      identify other traffic on the user device wherein the other traffic is associated with a nonsecure function of a noncertified application,
      determine that the nonsecure function does not require security,
      allow the noncertified application to run in the nonsecure environment,
   a nonsecure environment memory coupled to the nonsecure environment processor;
   at least one of a Bluetooth radio, a Bluetooth Low Energy radio and a WiFi radio for communicating with the medical device, wherein the at least one of the Bluetooth radio, the Bluetooth Low Energy radio and the WiFi radio is exclusively controlled by the secure environment processor when communicating with the medical device;
   a wide area network radio wherein the wide area network radio receives the certified medical application from a service platform;
   storing code for at least a portion of the certified medical application and code for a first operating system in the secure environment memory wherein the secure environment memory segment is isolated from the nonsecure environment memory and wherein the nonsecure environment memory is configured to store code for a second operating system and the noncertified applications, wherein:
      the first operating system supports execution of the certified medical application by the secure environment processor,
      the second operating system supports execution of the one or more noncertified applications,
      the first operating system operates independently of the second operating system wherein the first operating system remains operational when the second operating system is turned off or becomes non-operational or corrupted, and
      the non-certified applications do not interact with the secure environment memory; and
   initiating establishment of a communication link from the user device to the medical device via at least one of the Bluetooth radio, the Bluetooth Low Energy radio and the WiFi radio, wherein the communication link is configured to facilitate execution of the certified medical application.

2. The method of claim 1 further comprising sending, to the medical device, one or more instructions for execution on the medical device to implement a medical control or monitoring function.

3. The method of claim 1 further comprising receiving, from the medical device, a set of data associated with a control or monitoring function implemented on the medical device.

4. The method of claim 3 further comprising storing, in the secure memory segment, the set of data.

5. The method of claim 4 wherein the set of data is encrypted prior to storing.

6. The method of claim 4 further comprising sending, from the user device to a service platform, the set of data.

7. The method of claim 6 further comprising encrypting the set of data prior to the sending the set of data.

8. The method of claim 1 further comprising verifying that the certified medical application conforms to one or more regulatory requirements.

9. The method of claim 8 wherein the verifying including validating that the certified medical application conforms to a Food and Drug Administration (FDA) medical device compliance regulation.

10. A computer implemented method of operating a medical device, comprising:
    initiating establishment of a communications connection between a user device and the medical device wherein the user device includes:
    a secure environment processor included within a secure environment of the user device wherein the secure environment is provided with guaranteed processor and memory resources in the event of at least one of a denial of service attack and an attempt to overload processing or memory usage in the secure environment,
    a nonsecure environment processor wherein the secure environment processor is physically isolated from the nonsecure environment processor,
    a secure environment memory coupled to the secure processor and accessible only to the secure environment processor, the secure environment memory being included within the secure environment and including a security monitor executed by the secure environment processor wherein the security monitor is configured to:

identify secure traffic on the user device wherein the secure traffic is associated with a function of the certified medical application requiring security, identify a security requirement associated with the function, manage execution of the certified medical application within the secure environment in accordance with the security requirement, identify other traffic on the user device wherein the other traffic is associated with a nonsecure function of a noncertified application, determine that the nonsecure function does not require security, allow the noncertified application to run in the nonsecure environment, a nonsecure environment memory coupled to the nonsecure environment processor;

at least one of a short range wireless radio and a wired connector for facilitating the communications connection;

at least one of an LTE radio and a WiFi radio configured to receive a certified medical application from a service platform;

sending, from the certified medical application and via the communications connection, instructions for controlling or monitoring an operational function of the medical device, wherein:

the secure environment memory is configured to store code for a first operating system and the certified medical application, the nonsecure environment memory is configured to store one or more nonsecure applications and code for a second operating system, the first operating system supporting execution of the certified medical application, the second operating system supporting execution of the one or more noncertified applications, the first operating system operates independently of the second operating system, and the non-certified applications do not interact with the secure memory segment;

receiving, from the medical device and using the certified medical application, data associated with operation of the medical device; and storing the data associated with operation of the medical device in the secure environment memory.

11. The method of claim 10 further including sending, from the user device, the data associated with operation of the medical device to a service platform.

12. The method of claim 10 wherein the sending further includes sending another certified medical application to the medical device.

13. An apparatus for a user device, comprising:

a secure environment processor included within a secure environment of the user device wherein the secure environment is provided with guaranteed processor and memory resources in the event of at least one of a denial of service attack and an attempt to overload processing or memory usage in the secure environment;

a nonsecure environment processor wherein the secure environment processor is physically isolated from the nonsecure environment processor;

a nonsecure environment memory coupled to the nonsecure environment processor wherein the nonsecure environment memory is configured to store code for a first operating system and one or more non-certified applications;

a secure environment memory coupled to the secure processor and accessible only to the secure environment processor wherein the secure environment memory is configured to securely store code for a second operating system and a certified medical application disposed for execution on the secure environment processor to facilitate control and/or monitoring of a medical device;

at least one of a Bluetooth radio, a Bluetooth Low Energy radio and a WiFi radio for communicating with the medical device, wherein the at least one of the Bluetooth radio, the Bluetooth Low Energy radio and the WiFi radio is exclusively controlled by the secure environment processor when communicating with the medical device;

at least one of a wide area network radio and a wired connector wherein the at least one of a wide area network radio and the wired connector receives the certified medical application from a service platform;

wherein the second operating system supports execution of the certified medical application and the first operating system supports execution of one or more noncertified applications, and further wherein:

the first operating system operates independently of the second operating system, the second operating system boots prior to booting the first operating system, and the non-certified applications do not interact with the secure environment memory.

14. The apparatus of claim 13 wherein the secure environment memory—is further configured to securely store a set of data provided from the medical device.

15. The apparatus of claim 13 wherein the secure environment memory further includes a secure communication application configured to receive, from the service platform, the certified medical application and store the certified medical application in the secure environment memory.

16. The apparatus of claim 15 wherein the secure communication application is further configured to verify, in response to receipt of the medical application, that the received medical application has been approved for operation with the medical device by a regulatory authority.

17. The apparatus of claim 16 wherein the regulatory authority is the FDA.

18. A medical device, comprising:

a sensor configured to monitor at least one physiological characteristic of a patient;

a secure environment processor coupled to the sensor, wherein the secure environment processor is included within a secure environment of the user device and wherein the secure environment is provided with guaranteed processor and memory resources in the event of at least one of a denial of service attack and an attempt to overload processing or memory usage in the secure environment;

a nonsecure environment processor wherein the secure environment processor is physically isolated from the nonsecure environment processor;

a nonsecure environment memory coupled to the nonsecure environment processor wherein the nonsecure environment memory is configured to store code for a first operating system and one or more noncertified applications;

a secure environment memory being included within the secure environment and being coupled to the secure processor and accessible only to the secure environment processor wherein the secure environment memory is configured to securely store code for a second operating system and a certified medical application disposed for execution on the secure environment processor to facilitate monitoring of the physiological characteristic and wherein the secure environment memory includes a security monitor executed by the secure environment processor wherein the security monitor is configured to:
 identify secure traffic on the medical device wherein the secure traffic is associated with a function of the certified medical application requiring security,
 identify a security requirement associated with the function,
 manage execution of the certified medical application within the secure environment in accordance with the security requirement;
at least one of a Bluetooth radio, a Bluetooth Low Energy radio and a WiFi radio for communicating with a user device, wherein the at least one of the Bluetooth radio, the Bluetooth Low Energy radio and the WiFi radio is exclusively controlled by the secure environment processor when communicating with the user device; wherein:
 the second operating system supports execution of the certified medical application and boots before booting of the first operating system,
 the first operating system supports execution of the one or more noncertified applications,
 the first operating system operates independently of the second operating system, and
 the non-certified applications do not interact with the secure environment memory.

19. The device of claim 18 wherein the secure environment memory is further configured to securely store a set of data provided from the sensor.

20. The device of claim 19 wherein the memory further includes a secure communication application configured to receive, from a service platform, a certified medical application and store the certified medical application in the secure environment memory.

21. The device of claim 20 wherein the secure communication application is further configured to verify, in response to receipt of the medical application, that the received certified medical application has been approved for operation with the medical device by a regulatory authority.

22. The device of claim 21 wherein the regulatory authority is the FDA and the certified medical application has been certified by the FDA.

23. The method of claim 1 wherein the nonsecure environment memory includes first data and the secure environment memory includes second data, the first data being securely partitioned from the second data.

24. The method of claim 1 wherein the secure environment memory is configured to support a first secure environment and a second secure environment, the first secure environment being securely partitioned from the second secure environment and including the certified medical application.

25. The method of claim 24 wherein the second secure environment includes another certified medical application.

26. The method of claim 1 further including booting the first operating system prior to booting the second operating system.

27. The method of claim 1, further comprising setting priority to execute the certified medical application over one or more of the non-certified applications.

28. An apparatus for a user device configured to interact with a medical device and a service platform, the apparatus comprising:
 a secure environment processor wherein the secure environment processor is included within a secure environment and comprises one of an ARM core and an x86 processor core wherein the secure environment is provided with guaranteed processor and memory resources in the event of at least one of a denial of service attack and an attempt to overload processing or memory usage in the secure environment;
 a nonsecure environment processor wherein the secure environment processor is at least one of physically and virtually isolated from the nonsecure environment processor;
 a nonsecure environment memory coupled to the nonsecure environment processor wherein the nonsecure environment memory is configured to store code for a first operating system and one or more non-certified applications;
 a secure environment memory coupled to the secure processor and accessible only to the secure environment processor wherein the secure environment memory is configured to securely store code for a second operating system and a certified medical application disposed for execution on the secure environment processor to facilitate control and/or monitoring of a medical device and wherein the secure environment memory includes a security monitor executed by the secure environment processor wherein the security monitor is configured to:
  identify secure traffic wherein the secure traffic is associated with a function of the certified medical application requiring security,
  identify a security requirement associated with the function,
  manage execution of the certified medical application within the secure environment in accordance with the security requirement;
 at least one of a short range radio and a wired connector for communicating with the medical device;
 at least one of a wide area network radio and a wired connector wherein the at least one of a wide area network radio and the wired connector receives the certified medical application from the service platform;
 wherein the second operating system supports execution of the certified medical application and the first operating system supports execution of one or more non-certified applications, and further wherein:
  the first operating system operates independently of the second operating system wherein the secure environment is configured such that the second operating system continues to run when the first operating system becomes corrupted or is turned off, and
  the non-certified applications do not interact with the secure environment memory.

29. An apparatus for a user device configured to interact with a medical device and a service platform, the apparatus comprising:
 a first processor element;
 a second processor element;
 a hardware-enabled security monitor configured to isolate secure traffic processed by the second processor element from the first processor element;

a first memory coupled to the first processor element wherein the first memory is configured to store code for a first operating system and one or more non-certified applications;

a second memory coupled to the second processor element and accessible only to the second processor element wherein the second memory is configured to securely store code for a second operating system and a certified medical application disposed for execution on the second processor to facilitate control and/or monitoring of a medical device and wherein the second memory includes a security monitor executed by the second processor element wherein the security monitor is configured to:

identify secure traffic wherein the secure traffic is associated with a function of the certified medical application requiring security, identify a security requirement associated with the function, manage execution of the certified medical application within the secure environment in accordance with the security requirement;

at least one of a short range radio and a wired connector for communicating with the medical device;

at least one of a wide area network radio and a wired connector wherein the at least one of a wide area network radio and the wired connector receives the certified medical application from the service platform;

wherein the second operating system supports execution of the certified medical application and the first operating system supports execution of one or more non-certified applications, and further wherein:

the first operating system operates independently of the second operating system such that the second operating system continues to run when the first operating system becomes corrupted or is turned off, and the non-certified applications do not interact with the second memory;

wherein the second memory and the second operating system are included within a secure environment and the secure environment is provided with guaranteed processor and memory resources in the event of at least one of a denial of service attack and an attempt to overload processing or memory usage in the secure environment.

30. The method of claim 1 wherein the security monitor identifies the secure traffic by looking for traffic on the user device that is flagged as requiring security.

31. The method of claim 30 wherein a predefined bit is set in packets of the secure traffic and the predefined bit is not set in packets of the other traffic.

* * * * *